(12) United States Patent
Gokaraju et al.

(10) Patent No.: US 8,828,377 B2
(45) Date of Patent: *Sep. 9, 2014

(54) BOSWELLIA OIL, ITS FRACTIONS AND COMPOSITIONS FOR ENHANCING BRAIN FUNCTION

(75) Inventors: Ganga Raju Gokaraju, Vijayawada (IN); Rama Raju Gokaraju, Vijayawada (IN); Venkata Kanaka Ranga Raju Gokaraju, Vijayawada (IN); Trimurtulu Golakoti, Vijayawada (IN); Kiran Bhupathiraju, Vijayawada (IN); Venkata Krishna Raju Alluri, Vijayawada (IN)

(73) Assignee: Laila Nutraceuticals, Vijayawada, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/616,283

(22) Filed: Sep. 14, 2012

(65) Prior Publication Data

US 2013/0045183 A1 Feb. 21, 2013

Related U.S. Application Data

(63) Continuation-in-part of application No. PCT/IN2011/000170, filed on Mar. 14, 2011, and a continuation-in-part of application No. PCT/IN2011/000364, filed on May 26, 2011.

(30) Foreign Application Priority Data

Mar. 15, 2010 (IN) .............................. 687/CHE/2010
May 30, 2010 (IN) .............................. 688/CHE/2010

(51) Int. Cl.
*A01N 63/00* (2006.01)
*A61K 36/00* (2006.01)
*A61K 36/324* (2006.01)
*A61K 35/60* (2006.01)

(52) U.S. Cl.
CPC ............... *A61K 36/324* (2013.01); *A61K 35/60* (2013.01)

USPC .......................................... 424/93.1; 424/725

(58) Field of Classification Search
USPC ................................. 424/93.1, 725
See application file for complete search history.

(56) References Cited

U.S. PATENT DOCUMENTS 5,629,351 A 5/1997 Taneja et al.
5,665,386 A 9/1997 Benet et al.
(Continued)

FOREIGN PATENT DOCUMENTS

DE 10041217 3/2002
WO 02/15916 2/2002

OTHER PUBLICATIONS

International Search Report dated Aug. 30, 2011 issued for International Application No. PCT/IN2011/000170.

(Continued)

*Primary Examiner* — Karen Cochrane Carlson
*Assistant Examiner* — Jennifer M. H. Tichy
(74) *Attorney, Agent, or Firm* — Kramer Amado, P.C.

(57) ABSTRACT

The present disclosure relates to non-acidic extracts or fractions selected from a *Boswellia* low polar gum resin extract fraction (BLPRE), a *Boswellia* volatile oil fraction (BVOIL), and a *Boswellia* oil fraction (BOIL) and their compositions. BLPRE, BOIL, and BVOIL are each derived from the gum resin of a *Boswellia* species. These compositions are useful for improving mental condition, enhancing brain functions such as cognition, memory, learning, communication and brain health, for treating impaired memory, and for preventing, control or treating memory and cognition related disorders/diseases. Additionally, BOIL, BVOIL, and mixtures of BOIL and BVOIL are useful for enhancing the bioavailability of a biological agent.

35 Claims, 8 Drawing Sheets

(56) References Cited

U.S. PATENT DOCUMENTS

| | | | |
|---|---|---|---|
| 5,720,975 | A | 2/1998 | Etzel et al. |
| 2006/0089409 | A1 | 4/2006 | Gokaraju et al. |
| 2006/0177467 | A1 | 8/2006 | Mack et al. |
| 2006/0280811 | A1 | 12/2006 | Bombardelli |
| 2007/0248693 | A1 | 10/2007 | Mazzio et al. |
| 2008/0275117 | A1 | 11/2008 | Li et al. |
| 2008/0292736 | A1 | 11/2008 | Qazi et al. |
| 2009/0318551 | A1 | 12/2009 | Gokaraju et al. |

OTHER PUBLICATIONS

International Search Report dated Dec. 1, 2011 issued for International Application No. PCT/IN2011/000364.

Aarsland, et al., "Role of Cholinesterase Inhibitors in Parkinson's Disease and dementia with Lewy Bodies", J Beriatr Psychiatry Neural 2004; 17; 164.

Berg, et al, "The Additive Contribution from Inflammatory Genetic Markers on the Severity of Cardiovascular Disease", Scandinavian Journal of Immunology 69, 36-42, 2009.

Cuaz-Perolin, et al., "Antiinflammatory and Antiatherogenic Effects of the NF-kB Inhibitor Acetyl-11-Keto-B-Boswellic Acid in LPSm Challenged ApoE-/-Mice", Arterioscler Thromb Vasc Biol. 2008; 28:272-277.

Cullen, et al., "The nucleus basalis (Ch4) in the alcoholic Wernicke-Korsakoff syndrome: reduced cell number in both amnesic and non-amnesic patients", Journal of Neurology, Neurosurgery, and Psychiatry 1997;63:315-320.

Ernst, , "Frankincense: systematic review", BMJ 2008:337:a2813.

Halliday, et al., "Neuropathological correlates of memory dysfunction in the Wernicke-Korsakoff syndrome", Alcohol Alcohol Suppl. 1994;2:245-51.

Kimmatkar, et al., "Efficacy and tolerability of *Boswellia serrata* extract in treatment of osteoarthritis of knee—A randominzed double blind placebo controlled trial", Phytomedicine 10: 3-7 (2003).

Knight, et al., "Protease-activated receptors in human airways: Upregulation of PAR-2 in respiratory epithelium from patients with asthma", J Allergy Clin Immunol 2001:108:797-803.

Lee, et al., "Acetylcholinesterase Inhibitors from the Twigs of Vaccinium oldhami Miguel", Arch Pharm Res vol. 27, No. 1, 53-56, 2004.

Mancini, et al., "5-Lipoxygenase-activating protein is an arachidonate binding protein", FEBS 12163 vol. 318, No. 3, 277-281, 1993.

Moussaieff, et al., "Incensole Acetate, a Novel Anti-Inflammatory Compound Isolated from *Boswellia* Resin, Inhibits Nuclear Factor-kB Activation", Molecular Pharmacology 72: 1657-1664, 2007.

Roy, et al., "Human Genome Screen to Identify the Genetic Basis of the Anti-inflammatory Effects of *Boswellia* in Microvascular Endothelial Cells", DNA and Cell Biology, vol. 24, No. 4, 2005, pp. 244-255.

Safayhi, et al., "Inhibition by Boswellic Acids of Human Leukocyte Elastase", JPET 281:460-463, 1997.

Sailer, et al., "Acetyl-11-keto-Beta-boswellic acid (AKBA): structure requirements for binding and 5-lipoxygenase inhibitory activity", British Journal of Pharmacology (1996) 117,615-618.

Singh, et al., "Boswellic acids: A leukotriene inhibitor also effective through topical application in inflammatory disorders", Phytomedicine 15 (2008) 400-407.

Werber, et al., "The beneficial effect of cholinesterase inhibitors on patients suffering from Parkinson's disease and dementia", J Neural Transm (2001) 108:1319-1325.

Zutshi, et al., "Mechanism of Cholesterol Lowering Effect of Salai Guggal Ex. *Boswellia serrata* ROXB", Indian J. Pharmac.—18:182-183, 1986.

A: chromatogram at 252 nm

B: chromatogram at 210 nm

A

B

C

A

B

BOSWELLIA OIL, ITS FRACTIONS AND COMPOSITIONS FOR ENHANCING BRAIN FUNCTION

CROSS-REFERENCE TO RELATED APPLICATIONS

This application is a continuation-in-part of international application PCT/IN2011/000170, filed on Mar. 14, 2011, which claims priority to Indian patent application 687/CHE/2010, filed Mar. 15, 2010; and also a continuation-in-part of international application PCT/IN2011/000364, filed on May 26, 2011, which claims priority to Indian patent application 688/CHE/2010, filed May 30, 2010. The entire disclosures of the prior applications are hereby incorporated by reference in their entirety.

FIELD OF THE DISCLOSURE

The current disclosure provides non-acidic *Boswellia* low polar gum resin extract fraction (BLPRE), *Boswellia* volatile oil fraction (BVOIL) and *Boswellia* oil fraction (BOIL) comprising BLPRE and BVOIL individually and their composition(s) obtained by combining with at least one biological agent or Nootropic agent for the prevention, control and treatment of brain related diseases comprising Attention-deficit Hyperactivity Disorder (ADHD) and memory deficits or to enhance brain functions such as cognition, memory, learning and communication Importantly, the above fractions and compositions of the present disclosure help in improving brain health, brain function, and memory.

The current disclosure also provides a non-acidic *Boswellia* low polar gum resin extract fraction (BLPRE), a *Boswellia* volatile oil fraction (BVOIL), or a *Boswellia* oil fraction (BOIL) comprising BLPRE and BVOIL for increasing the bioavailability of biological agents. According to the current disclosure, BLPRE and BVOIL may be prepared by fractionation of BOIL.

BACKGROUND OF THE DISCLOSURE

The gum resin of *Boswellia serrata* (Burseraceae) plant has long been in use for the treatment of several diseases by the practitioners of Ayurvedic medicines in the Indian system of medicine. The extract of *Boswellia* was found to be a potent anti-inflammatory and anti-arthritic agent. The origin of anti-inflammatory actions of *Boswellia* gum resin and its extracts has been attributed to a group of triterpene acids called boswellic acids that were isolated from the gum resin of *Boswellia serrata*. Boswellic acids exert anti-inflammatory actions by inhibiting 5-lipoxygenase (5-LOX). 5-LOX is a key enzyme for the biosynthesis of leukotrienes from arachidonic acid. 3-O-Acetyl-11-keto-β-boswellic acid (AKBA) is biologically the most active component among its congeners, it being able to inhibit 5-LOX with an $IC_{50}$ of 1.5 µM.

*Boswellia* gum resin and its extracts also demonstrated significant therapeutic improvements in human clinical trials confirming the anti-inflammatory effects shown in vitro and in vivo.

Worldwide aging of the population has increased the incidents of cognitive deficits, such as age-associated memory impairment and senile dementias, and this causes great disruptive impact on the life of the affected individuals. The "cholinergic hypothesis of learning" played a pivotal role in the development of drugs for degenerative diseases.

A disturbance of the cortical cholinergic system accompanied by a reduction of choline acetylase (reduced acetylcholine synthesis) is inter alia detectable biochemically in case of neurological diseases. Hence, there is a demand for a medicament whose active substance can ameliorate this disturbance and highly available at the target organ (brain) and which is well tolerated, particularly in long-term therapy.

Acetylcholinesterase (AChE) is an important enzyme to hydrolyze acetylcholine, a neurotransmitter mediating the activity of parasympathetic nerve, into choline and acetate. AChE is formed in the endoplasmic reticulum, and moves and functions in the cell membrane. AChE is distributed around cholinergic nerve, particularly much at the myoneural junction, and is found in the serum, liver and other tissues.

A wide range of evidence shows that acetylcholinesterase (AChE) inhibition can improve cognitive and mental functions through enhancing cortical cholinergic neurotransmission. The acetylcholinesterase (AChE) inhibitors increase the concentration of acetylcholine and help nerve cells to communicate better. The longer acetylcholine remains in the brain, the longer those cells can call up memories. The earliest known AChE inhibitors are physostigmine and tacrine.

However, clinical studies show that physostigmine has poor oral activity, brain penetration and pharmacokinetic parameters while tacrine has hepatotoxic side effects. Studies were thus focused on finding new types of acetylcholinesterase inhibitors that would overcome the disadvantages of these two compounds.

Donepezil and Rivastigmin inaugurate a new class of AChE inhibitors with longer and more selective action with manageable adverse effects but still small improvement of cognitive impairment. Galanthamine (Reminyl), an alkaloid isolated from *Galanthus nivalis*, is another recently approved AChE inhibitor for the treatment of Alzheimer's. It is selective, long acting, and reversible. Galanthamine produces beneficial effects in patients. Similarly, huperzine A, a novel *Lycopodium* alkaloid discovered from the Chinese medicinal plant *Huperzia serrata* is a potent, reversible and selective inhibitor of AChE with a rapid absorption and penetration into the brain in animal tests. It exhibits memory-enhancing activities in animal and also in clinical trials.

Dementia with Lewy bodies (DLB) is a common cause of dementia. Changes in the acetylcholine system have been reported in brains of patients with DLB, which provides a rational basis for trials of acetylcholinesterase inhibitors in DLB.

Current treatment of dementia in Parkinson's disease (PD) is based on the compensation of profound cholinergic deficiency, as in recent studies with the cholinesterase inhibitors galantamine, donepezil and rivastigmine. It has also been shown that cholinesterase inhibitors can improve motor function in PD. The beneficial effect of cholinesterase inhibitors has been studied on patients suffering from Parkinson's disease and dementia.

Studies show that Wernicke-Korsakoff syndrome is associated with a persisting severe anterograde amnesia in which memory is not transferred from short-to long-term storage. It is believed to be a consequence of a thiamine-deficient state often found in alcohol abusers. The memory deficit has been attributed to a number of brain lesions (corpus mamillare and dorsomedial nucleus of the thalamus), loss of cholinergic forebrain neurons and serotonin-containing neurons. Many studies and case-reports suggest efficacy of acetylcholinesterase inhibitors in the Wemicke-Korsakoff-associated memory deficit. Studies also suggest that neurons in the nucleus basalis are at risk in thiamine deficient alcoholic.

The U.S. Pat. No. 5,720,975 relates to the use of incense (olibanum), incense extracts, substances contained in incense, their physiologically acceptable salts, their derivatives and their physiological salts, pure boswellic acid, of physiologically acceptable salts, of a derivative, of a salt of the derivative, for production of a medicament for the prevention or treatment of Alzheimer's disease.

US publication US20060177467A1 relates to the use of the hydrogenation products of frankincense (olibanum), its hydrogenated ingredients as well as physiologically acceptable salts and derivatives thereof and hydrogenated frankincense extracts for the production of a medicament for the prophylactic and/or therapeutic treatment of cerebral ischemia, cranial/brain trauma and/or Alzheimer's disease.

There is currently no prior art, to the best of the Applicants' knowledge, relating to the use of *Boswellia* non-acidic oil fractions and their compositions for the prevention, control and treatment of Memory and Cognition related diseases and enhancing brain functions.

Additionally, there are numerous pharmaceutical ingredients, herbal ingredients and biologically active molecules that are effective in vitro against a disease condition or disorder. However, several of these ingredients are not effective or not bioavailable in vivo, i.e., after administration to warm blooded animals. It is thus important to explore and identify safe and effective agents that help to increase the bioavailability of such ingredients. As set forth in the present disclosure, *Boswellia* non-acidic oil fractions have been found to increase bioavailability of a number of extracts, fractions, phytochemicals and compounds originating from plant, animal or microorganism sources.

There is currently no prior art, to the best of the Applicants' knowledge, relating to the use of *Boswellia* non-acidic oil fractions and their compositions for increasing the bioavailability of biological agents in warm blooded animals.

SUMMARY OF THE DISCLOSURE

Various embodiments of the present disclosure provide use of compositions comprising *Boswellia* non-acidic fraction(s) selected from *Boswellia* low polar gum resin extract fraction (BLPRE) having a novel phytochemical composition, *Boswellia* volatile oil fraction (BVOIL), and a *Boswellia* oil fraction (BOIL) comprising BLPRE and BVOIL fractions, either individually or in combination. These compositions are useful for improving brain health and brain functions, which include but are not limited to cognition, memory, intelligence, motivation, attention, concentration, learning power and better communication. These compositions are also useful to alleviate disease conditions related to cognition and memory deficits and the like.

Various embodiments disclosed herein provide use of *Boswellia* non-acidic fraction(s) selected from *Boswellia* low polar gum resin extract fraction (BLPRE), *Boswellia* volatile oil fraction (BVOIL), and a *Boswellia* oil fraction (BOIL) comprising BLPRE and BVOIL, either individually or as compositions, to prevent, control and treat brain related diseases/disorders which include but not limited to senile dementia, multi-infarct dementia, dyslexia, aphasia, organic brain syndrome, myasthenia gravis, vascular dementia, mild cognitive impairment (MCI), Lewy body dementia, Wernicke-Korsakoff-syndrome, Alzheimer's, Parkinson's disease, Attention-deficit Hyperactivity Disorder (ADHD), hypoxia, anoxia, cerebrovascular insufficiency, epilepsy, myoclonus and hypocholinergic dysfunctions, to slowdown memory deterioration, functional loss and to treat memory impairment disorders, neurodegenerative disorders, and for controlling blood pressure and blood circulation in the brain.

Various embodiments disclosed herein relate to compositions comprising at least one component selected from *Boswellia* low polar gum resin extract fraction (BLPRE), *Boswellia* volatile oil fraction (BVOIL) and non-acidic *Boswellia* oil fraction consisting of BLPRE and BVOIL in combination with at least one component selected from biological agent(s), Nootropic agent(s).

In another aspect, the disclosure provides compositions comprising at least one component selected from *Boswellia* low polar gum resin extract fraction (BLPRE), *Boswellia* volatile oil fraction (BVOIL) and non-acidic *Boswellia* oil fraction (BOIL) consisting of BLPRE and BVOIL in combination with at least one component selected from *Boswellia* extract(s), fraction(s), extracts/fractions enriched in one or more boswellic acids, their salts or derivatives thereof.

In another aspect, the disclosure provides compositions comprising at least one component selected from *Boswellia* low polar gum resin extract fraction (BLPRE), *Boswellia* volatile oil fraction (BVOIL) and non-acidic *Boswellia* oil fraction (BOIL) in combination with one or more agents selected from natural antioxidants, anti-inflammatory agents and immune modulators.

In another embodiment, the disclosure provides *Boswellia* low polar gum resin extract fraction (BLPRE) for increasing the bioavailability of biological agents.

In further embodiments, the disclosure provides compositions comprising at least one component selected from *Boswellia* oil (BOIL), *Boswellia* volatile oil (BVOIL) and *Boswellia* low polar gum resin extract (BLPRE) obtained from *Boswellia* gum resin in combination with a biological agent, for increasing the bioavailability of biological agents in warm blooded animals in need thereof.

In various embodiments, the disclosure provides *Boswellia* derived bioenhancing agents for increasing the bioavailability of one or more biological ingredients or functional ingredients.

In certain embodiments, the disclosure provides *Boswellia* derived bioenhancing agents for increasing the bioavailability of one or more pharmaceutical drugs/synthetic drugs.

In various embodiments, the disclosure provides *Boswellia* derived bioenhancing agents for increasing the bioavailability of one or more *Boswellia* derived components.

In various embodiments, the disclosure provides non-acidic *Boswellia* derived bioenhancing agents for increasing the bioavailability of one or more acidic *Boswellia* derived components.

In certain embodiments, the disclosure provides *Boswellia* derived bioenhancing agents for increasing the bioavailability of one or more *Curcuma* derived components.

In various embodiments disclosed herein, a non-acidic *Boswellia* oil fraction selected from the group consisting of an intact *Boswellia* oil (BOIL) and a *Boswellia* volatile oil (BVOIL) may be produced by:
a. procuring the gum resin of a plant of the genus *Boswellia*;
b. extracting said gum resin with a non-polar organic solvent to produce a non-polar solvent extract solution;
c. washing the non-polar solvent extract solution with an alkali solution to remove acidic compounds from the non-polar solvent extract solution;
d. washing the non-polar solvent extract solution successively with water and brine;
e. evaporating non-polar solvent from the non-polar solvent extract solution to obtain BOIL as an oily residue; and optionally
f. isolating volatile components from BOIL as BVOIL.

DETAILED DESCRIPTION

A. Definitions

Figure 1:
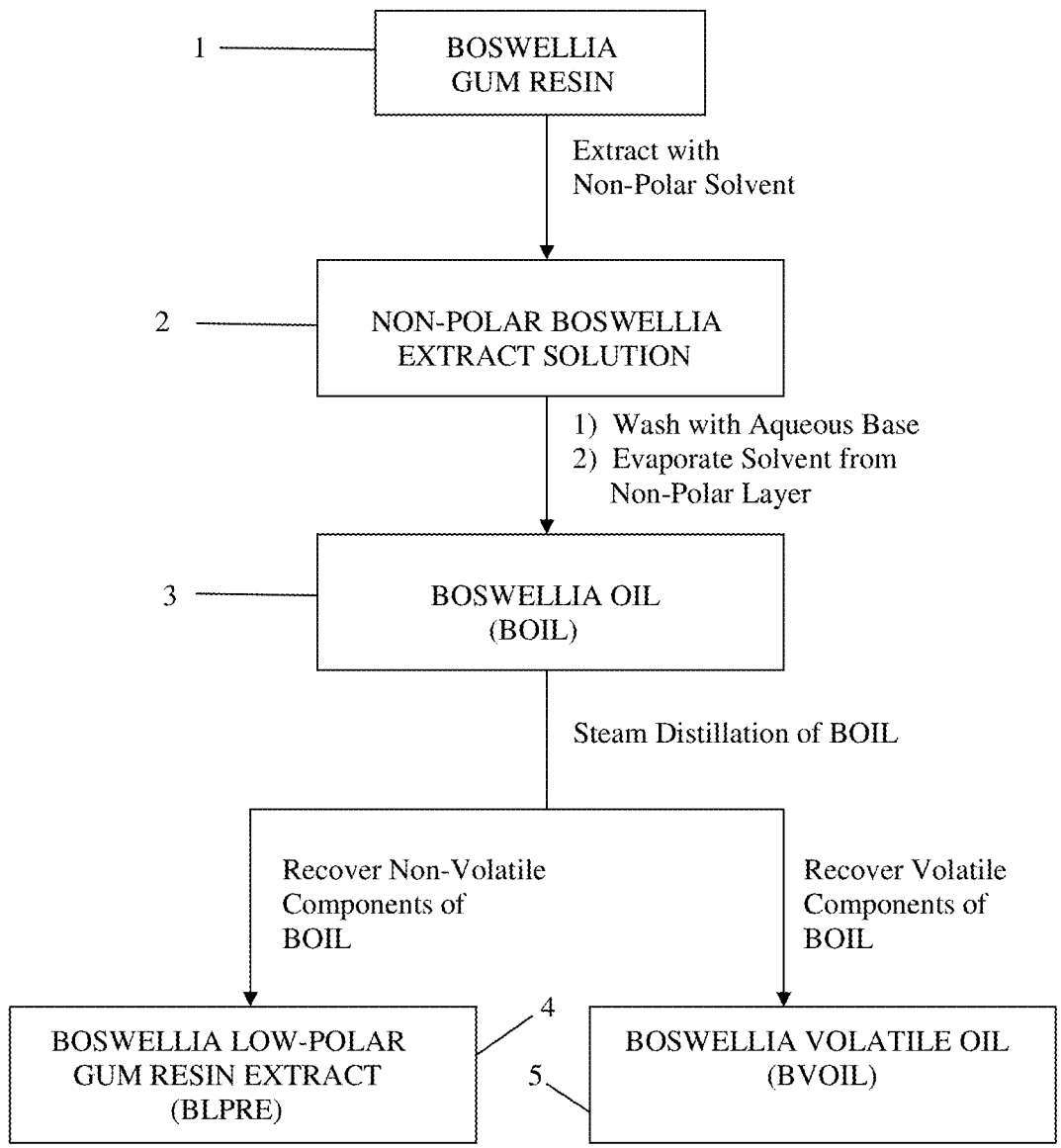
FIGS. 1 and 2 show processes for obtaining BLPRE, BOIL, and BVOIL.
Figure 2:
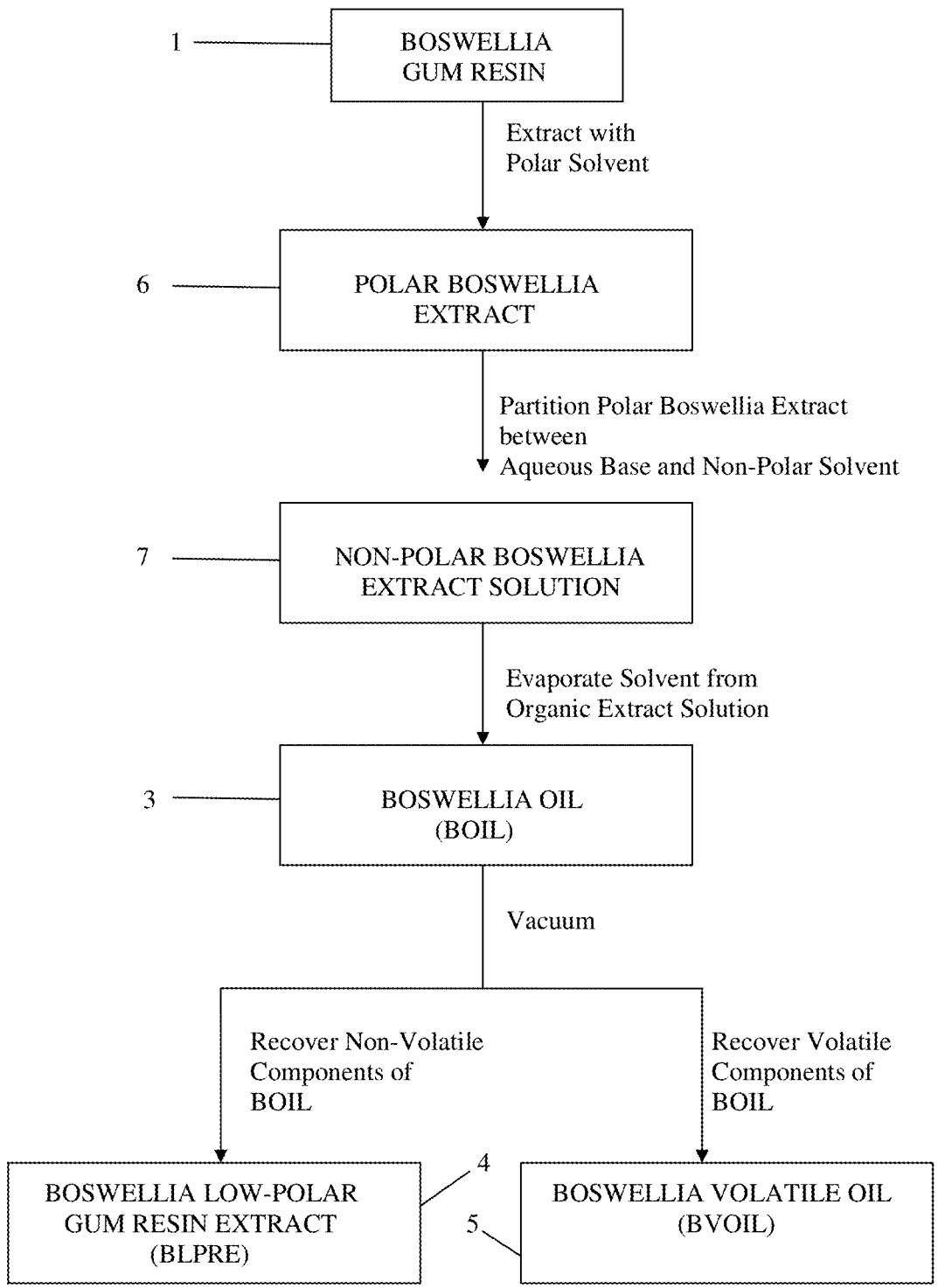

1. '*Boswellia* oil' or 'non-acidic *Boswellia* extract' or 'BOIL' used herein refers to non-acidic *Boswellia* gum resin extract containing non-acidic *Boswellia* low polar gum resin extract fraction (BLPRE) and *Boswellia* volatile oil fraction (BVOIL) obtained from gum resin of any of the *Boswellia* species. BOIL encompasses 'BsOIL' and 'BcOIL,' as defined below.
2. '*Boswellia serrata* oil' or 'non-acidic *Boswellia serrata* extract' or 'BsOIL' used herein refers to non-acidic *Boswellia serrata* gum resin extract containing non-acidic *Boswellia serrata* low polar gum resin extract fraction (BsLPRE) and *Boswellia serrata* volatile oil fraction (BsVOIL) obtained from gum resin of the *Boswellia serrata* species.
3. '*Boswellia carterii* oil' or 'non-acidic *Boswellia carterii* extract' or 'BcOIL' used herein refers to non-acidic *Boswellia carterii* gum resin extract containing non-acidic *Boswellia carterii* low polar gum resin extract fraction (BcLPRE) and *Boswellia carterii* volatile oil fraction (BcVOIL) obtained from gum resin of the *Boswellia carterii* species.
4. '*Boswellia* low polar gum resin extract fraction' or '*Boswellia* low polar gum resin extract' or 'BLPRE' used herein refers to non-acidic *Boswellia* gum resin extract oil fraction comprising sesquiterpenes, diterpenes, triterpenes and other oily phytochemicals obtained after removing the volatile components from *Boswellia* oil obtained from gum resin of any of the *Boswellia* species by any of the processes described. BLPRE encompasses 'BsLPRE' and 'BcLPRE,' as defined below.
5. '*Boswellia serrata* low polar gum resin extract fraction' or '*Boswellia serrata* low polar gum resin extract' or 'BcLPRE' used herein refers to non-acidic *Boswellia serrata* gum resin extract oil fraction comprising sesquiterpenes, diterpenes, triterpenes and other oily phytochemicals obtained after removing the volatile components from *Boswellia* oil obtained from gum resin of *Boswellia serrata* species by any of the processes described.
6. '*Boswellia carterii* low polar gum resin extract fraction' or '*Boswellia carterii* low polar gum resin extract' or 'BcLPRE' used herein refers to non-acidic *Boswellia carterii* gum resin extract oil fraction comprising sesquiterpenes, diterpenes, triterpenes and other oily phytochemicals obtained after removing the volatile components from *Boswellia carterii* oil obtained from gum resin of *Boswellia carterii* species by any of the processes described.
7. '*Boswellia* volatile oil fraction' or '*Boswellia* volatile oil' or 'volatile oil' or 'volatile fraction' or 'BVOIL' used herein refers to the volatile fraction/extract comprising monoterpenes, sesquiterpenes, volatile oils and other oily phytochemicals obtained from gum resin of any of the *Boswellia* species by any of the processes described. BVOIL encompasses 'BsVOIL' and 'BcVOIL,' as defined below.
8. '*Boswellia serrata* volatile oil fraction' or '*Boswellia serrata* volatile oil' or 'serrata volatile oil' or 'serrata volatile fraction' or 'BsVOIL' used herein refers to the volatile fraction/extract comprising monoterpenes, sesquiterpenes, volatile oils and other oily phytochemicals obtained from gum resin of the *Boswellia serrata* species by any of the processes described.
9. '*Boswellia carterii* volatile oil fraction' or '*Boswellia carterii* volatile oil' or 'carterii volatile oil' or 'carterii volatile fraction' or 'BcVOIL' used herein refers to the volatile fraction/extract comprising monoterpenes, sesquiterpenes, diterpenes, volatile oils and other oily phytochemicals obtained from gum resin of the *Boswellia carterii* species by any of the processes described.
10. 'Gum' or 'Gum resin' or 'resin' used herein refers to an exudate of *Boswellia* plant species.
11. 'Phytochemical' refers to a pure or semi-pure compound or compounds isolated from plants.
12. Cognition refers to acquisition, processing and retention of information.
13. Cognition enhancer(s) refers to substance(s) that enhances concentration and memory.
14. Nootropic agent(s) refers to smart drugs, memory enhancers and cognitive enhancers, dietary supplements, nutraceuticals, functional ingredients and functional foods that are purported to improve mental functions such as cognition, memory, intelligence, motivation, attention and concentration.
15. Biological agent(s) refer to one or more agents selected from biologically active ingredient(s), anti-oxidant(s), dietary supplements, herbal ingredients, nutraceuticals, functional ingredients, functional foods and nootropic agents and oil(s) their mixtures obtained from plant(s)/animal(s)/microorganism(s)/synthesis or semi synthesis.
16. 'Biologically active ingredient(s)' refers to any pharmaceutically or dietetically acceptable active ingredient(s); compound(s), extract(s), fraction(s), phytochemical(s), synthetic drug(s) or their salts or mixtures thereof derived from plants, animals or microorganisms or obtained by chemical synthesis/semi-synthesis.
17. 'Functional ingredient(s)' refers to any herbal ingredients, dietary supplements, antioxidants, vitamins, minerals, amino acids, fatty acids, essential oils, fish oils, enzymes, glucosamine, Chondroitin and probiotics or their salts or mixtures thereof derived from plants or animals or microorganisms or chemical synthesis or semi-synthesis.
18. 'Bioenhancer(s)' refers to agents that enhance the availability of biological agent(s) through one or more mechanism(s) in warm blooded animals comprising increasing the bioavailability, enhancing the serum concentration, improving gastrointestinal absorption, improving systemic utilization, improving cross over through certain biological barriers such as respiratory lining, urinary lining, blood brain barrier and skin.
19. 'Bioenhancing composition(s)' refer to compositions comprising *Boswellia* derived oil fraction as a Bioenhancer in combination with one or more biological agent(s).
20. 'BSE 85%' used herein refers to *Boswellia serrata* extract standardized to 85% Boswellic acids.
21. 'BCE 85%' used herein refers to *Boswellia carterii* extract standardized to 85% Boswellic acids.
22. 'CLE 95%' refers to *Curcuma longa* extract standardized to 95% Curcuminoids.
23. 'CAE 20%' refers to *Curcuma aromatica* extract standardized to 20% Curcuminoids.

B. Use of *Boswellia* Non-Acidic Extracts in Enhancing Memory and Brain Function The gum resin of *Boswellia* has been very widely used since ancient times. The gum resin of various species of *Boswellia* such as *Boswellia serrata, Boswellia carterii* or *Boswellia papyrifera* is a complex mixture comprising *Boswellia* oil fraction (BOIL) containing essential oil/*Boswellia* volatile oil fraction (BVOIL) and non-acidic *Boswellia* low polar gum resin extract fraction (BLPRE); boswellic acids, sugars and polysaccharide fraction. The *Boswellia serrata/Boswellia carterii/Boswellia papyrifera* extracts widely available in the international markets are acidic fractions separated from the gum resin which are standardized to contain 65% or 85% total Boswellic acids by titrimetric method of analysis. During the execution of commercial process for regular *Boswellia* extracts derived from *Boswellia serrata/Boswellia carterii/Boswellia papyrifera* (85% total Boswellic acids), the acidic fraction, which contains predominantly triterpene acids including Boswellic acids is separated from the rest of gum resin components. The sugars and other polymeric materials get separated out into the aqueous phase during the enrichment process for total Boswellic acids. The remaining water immiscible low polar compounds are separated as *Boswellia* oil fraction/extract. These low polar compounds are either absent or present at very low concentration in both, commercial *Boswellia* extracts standardized to boswellic acids and *Boswellia* extracts selectively enriched in 3-O-acetyl-11-keto-β-Boswellic acid (AKBA).

The *Boswellia* non-acidic oil fractions BOIL, BVOIL, and BLPRE may be obtained in a number of ways. One method of obtaining the *Boswellia* non-acidic oil fractions BOIL, BVOIL, and BLPRE is outlined in FIG. 1. According to this method, *Boswellia* gum resin 1 is extracted with a non-polar or water-immiscible solvent to produce a solution of an extract of *Boswellia* gum resin 2 in a non-polar solvent. The non-polar solvent may be a non-polar organic solvent, such as 1,2-dichloroethane, hexane, dichloromethane, chloroform, ethyl acetate, n-butanol, or methyl iso-butyl ketone (MIBK). Alternatively, the non-polar solvent may be a non-polar inorganic solvent. The non-polar extract solution 2 is then washed with an aqueous base to extract boswellic acids and other acidic components into an aqueous layer, leaving a non-polar solvent layer containing non-acidic components of the extract of *Boswellia* gum resin. The non-polar solvent is then evaporated to produce a *Boswellia* oil (BOIL) 3, which contains volatile components and non-volatile components. BOIL 3 is subjected to steam distillation to volatilize the volatile components of BOIL 3. After removal of the volatile components from BOIL 3, the remaining non-volatile oil, here referred to as *Boswellia* low-polar gum resin extract (BLPRE) 4, may be recovered. Similarly, after steam distillation, the volatile components from BOIL 3 may be condensed or otherwise recovered as a *Boswellia* volatile oil (BVOIL) 5. Thus, BOIL 3 contains both volatile and non-volatile compounds. BLPRE 4 contains non-volatile compounds. BVOIL 5 contains only volatile compounds.

An alternative method of obtaining the *Boswellia* non-acidic oil fractions BOIL, BVOIL, and BLPRE is outlined in FIG. 2. According to this method, *Boswellia* gum resin 1 is extracted with a polar solvent, which may be alcohol or aqueous alcohol. The resulting polar *Boswellia* extract 6 is portioned between an aqueous base solution and a non-polar solvent to produce an aqueous layer and a non-polar solvent layer of a solution of an extract of *Boswellia* gum resin 7 in a non-polar solvent. The aqueous layer may be discarded. The non-polar solvent may be a non-polar organic solvent, such as 1,2-dichloroethane, hexane, dichloromethane, chloroform, ethyl acetate, n-butanol, or methyl iso-butyl ketone (MIBK). Alternatively, the non-polar solvent may be a non-polar inorganic solvent. The non-polar solvent is then evaporated from non-polar extract solution 7, leaving a *Boswellia* oil (BOIL) 3, which contains volatile components and non-volatile components. BOIL 3 is subjected to vacuum to volatilize the volatile components of BOIL 3. After removal of the volatile components from BOIL 3, the remaining non-volatile oil, here referred to as *Boswellia* low-polar gum resin extract (BLPRE) 4, may be recovered. Similarly, after steam distillation, the volatile components from BOIL 3 may be condensed or otherwise recovered as a *Boswellia* volatile oil (BVOIL) 5.

Process for Obtaining Non-Acidic *Boswellia* Oil (BOIL) Fraction:

A representative process for obtaining *Boswellia* oil comprises:

a) procuring the gum resin of one or more of the plant(s) selected from but not limited to *Boswellia serrata* or *Boswellia carterii* or *Boswellia papyrifera* or mixtures thereof,
b) extraction of the gum resin with a water immiscible organic solvent,
c) filtering the extract carefully to remove the insoluble resin material,
d) washing the organic solvent extract repeatedly with an aqueous alkali solution such as aqueous potassium hydroxide,
e) washing the organic layer with water and brine,
f) evaporating the organic layer under vacuum and high temperature to obtain the oily residue (BOIL).

Processes for Obtaining *Boswellia* Volatile Oil (BVOIL) Fraction:

The process for obtaining *Boswellia* volatile oil (BVOIL) is through steam distillation or using high vacuum from *Boswellia* gum resin.

A representative process for obtaining *Boswellia* volatile oil comprises:
a) procuring the gum resin of *Boswellia* and
b) separating the Volatile oil component by either steam distillation or distillation under high vacuum, low temperature from the said gum resin to obtain BVOIL.

In an alternative process,
a) BOIL is prepared according to the process described above,
b) BOIL is then subjected to steam distillation or vacuum distillation to collect *Boswellia* volatile oil (BVOIL)

Processes for Obtaining *Boswellia* Low Polar Gum Resin Extract (BLPRE) Fraction:

A representative procedure for obtaining *Boswellia* low polar gum resin extract (BLPRE) comprises:
a) extraction of the gum resin of *Boswellia* species with a water immiscible organic solvent and filtering the extract carefully to remove the insoluble resin material,
b) washing the organic solvent extract repeatedly with an aqueous alkali solution such as aqueous potassium hydroxide,
c) washing the organic layer obtained after the alkali wash, with water and brine,
d) evaporating the said organic layer under vacuum and high temperature to obtain the oily residue,
e) removing the volatile compounds from the said oily residue under high vacuum and very high temperature to obtain BLPRE.

Another representative procedure for obtaining *Boswellia* low polar gum resin extract (BLPRE) comprises:
a) preparing the alcohol or hydroalcohol extract of *Boswellia* gum resin,
b) partitioning the alcohol extract between an aqueous alkali solution and a water immiscible organic solvent,
c) separation of the organic solvent layer, followed by evaporation of the solvent to obtain oily residue,
d) removal of volatile compounds from the said oily residue under high temperature and high vacuum to obtain BLPRE.

Yet another representative procedure for obtaining *Boswellia* low polar gum resin extract (BLPRE) comprises:
a) extracting the gum resin of *Boswellia* species with alcohol or hydro alcohol,
b) evaporating the organic solvent to an optimum level of total solids and then
c) adjusting the pH to the alkaline side, preferably pH 9-12,
d) repeatedly extracting the solution with an organic solvent,
e) evaporating the organic solvent under vacuum and high temperature to obtain the oily residue,
f) evaporating the volatiles from the said oily residue under high vacuum and high temperature to obtain BLPRE as a non-volatile residue.

A representative procedure for obtaining *Boswellia serrata* volatile oil (BsVOIL) comprises:
a) procuring the gum resin of *Boswellia serrata*.
b) separating the Volatile oil component by either steam distillation or distillation under high vacuum, low temperature from the said gum resin to obtain BsVOIL.

Yet another representative procedure for obtaining *Boswellia carterii* volatile oil (BcVOIL) comprises:
a) procuring the gum resin of *Boswellia carterii*.
b) separating the Volatile oil component by either steam distillation or distillation under high vacuum, low temperature from the said gum resin to obtain BcVOIL.

The representative processes for obtaining *Boswellia* volatile oil (BVOIL) from *Boswellia serrata*, *Boswellia carterii* are described above. However, a similar process or processes can be applied to any of the gum resin obtained from *Boswellia* species for producing *Boswellia* volatile oil (BVOIL).

A representative procedure for obtaining *Boswellia serrata* low polar gum resin extract (BsLPRE) comprises:
a) Procuring the gum resin of *Boswellia serrata*.
b) extraction with an water immiscible organic solvent and the insoluble gum materials were separated by filtration and discarded,
c) washing the organic solvent extract repeatedly with dilute aqueous alkali solution to remove the acidic compounds,
d) washing the organic layer successively with water and brine,
e) evaporating the organic layer under vacuum at 60-70° C. to obtain an oily residue,
f) the volatile components are then removed from the said oily residue under high vacuum and very high temperature to obtain a viscous oil, which is referred herein after as *Boswellia serrata* low polar gum resin extract (BsLPRE).

Alternatively, the BsLPRE can also be prepared by a process comprising:
a) preparing the alcohol or hydroalcohol extract of *Boswellia serrata* gum resin,
b) partitioning the alcohol extract between an aqueous alkali solution and a water immiscible organic solvent,
c) separation of the organic solvent layer, followed by evaporating the organic layer under vacuum at 60-70° C. to obtain an oily residue,
d) the volatile components are then removed from the said oily residue under high vacuum and high temperature to obtain a viscous oil, which is referred herein after as *Boswellia serrata* low polar gum resin extract (BsLPRE).

A representative procedure for obtaining *Boswellia carterii* low polar gum resin extract (BcLPRE) comprises:
a) procuring the gum resin of *Boswellia carterii*,
b) extracting the gum resin with an water immiscible organic solvent and the insoluble gum materials were separated by filtration and discarded,
c) washing the organic solvent extract repeatedly with dilute aqueous alkali solution to remove the acidic compounds,
d) washing the organic layer successively with water and brine,
e) evaporating the organic layer under vacuum at 60-70° C. to obtain an oily residue.
f) the volatile components are then removed from the said oily residue under high vacuum and high temperature to obtain a viscous oil, which is referred herein after as *Boswellia carterii* low polar gum resin extract (BcLPRE).

Alternatively, the BcLPRE can also be prepared by process comprising:
a) preparing the alcohol or hydroalcohol extract of *Boswellia carterii* gum resin,
b) partitioning the alcohol extract between an aqueous alkali solution and a water immiscible organic solvent, c) separation of the organic solvent layer, followed by evaporating the organic layer under vacuum at 60-70° C. to obtain an oily residue, d) the volatile components are then removed from the said oily residue under high vacuum and high temperature to obtain a viscous oil, which is referred herein after as *Boswellia carterii* low polar gum resin extract (BcLPRE).

The representative processes for obtaining *Boswellia* low polar gum resin extract (BLPRE) from *Boswellia serrata* and *Boswellia carterii* are described above. However, a similar process or processes can be applied to any of the gum resin obtained from *Boswellia* species for producing the low polar gum resin extract.

In the above processes for obtaining BLPRE, BOIL, and/or BVOIL, the water immiscible organic solvent used for extraction of a *Boswellia* gum resin or for partitioning an alcohol extract may be, but is not limited to, 1,2-dichloroethane, hexane, dichloromethane, chloroform, ethyl acetate, n-butanol, methyl iso-butyl ketone (MIBK) or a suitable combination thereof. The alkali solution used for washing the organic solvent extract, or partitioning the alcohol extract, can be selected from Group-I or Group-II metal hydroxides, which include, but are not limited to, Sodium hydroxide, Potassium hydroxide, Calcium hydroxide, Magnesium hydroxide and mixtures thereof.

The said intact *Boswellia* oil (BOIL) or *Boswellia* volatile oil (BVOIL) or *Boswellia* low polar gum resin extract (BLPRE) constitute significant components in *Boswellia* gum resin. However, it has very limited commercial utility and it is mostly discarded as a waste material. Potential utilization of these fractions have been long overdue. It was found unexpectedly that *Boswellia serrata* low polar gum resin extract (BsLPRE), a fraction obtained after removing the volatile compounds from the *Boswellia serrata* oil, has several beneficial properties.

In our earlier Indian patent application 2229/CHE/2008 filed 15 Sep., 2008 and PCT application # PCT/IN2009/000505 filed 14 Sep., 2009 we disclosed synergistic compositions comprising AKBA enriched fraction and *Boswellia serrata* non-acidic extract (BNRE). BNRE composition and method of identification are also disclosed.

In our recent Indian patent application 394/CHE/2010 filed 15 Feb., 2010 we disclosed non Boswellic acid fraction and its synergistic compositions.

As a part of developing new agents for improving brain/mental function and alleviating disease conditions related to cognition and memory deficits, a large number of plant extracts have been screened for their inhibitory property on Acetylcholinesterase enzyme activity. The assay was performed in vitro by the method of Ellman et al., with minor modifications, using acetylthiocholine iodide as a substrate (Lee J. H., et. al. *Arch Pharm Res* 2004, 27(1): 53-56). It was found very unexpectedly that the non-acidic extract, *Boswellia serrata* oil (BsOIL), *Boswellia serrata* low polar gum resin extract (BsLPRE) fraction and *Boswellia serrata* volatile oil (BsVOIL) fractions, were potent inhibitors of acetylcholinesterase in vitro. BsLPRE for example potently inhibited acetylcholinesterase enzyme activity in vitro as shown in Table 2. BLPRE's in vitro efficacy against acetylcholinesterase enzyme is comparable to commercial drug Neostigmin. BsLPRE exhibited an IC50 value of 37.01 ng/mL compared to 43.29 ng/mL shown by neostigmin. Its acetylcholinesterase inhibitory activity was also evaluated by a cell based in vitro assay in Rat pheochromocytoma PC 12 cells. The inhibitory property of BsLPRE on the enzyme activity was assessed in β-amyloid peptide induced-rat pheochromocytoma PC 12 cells. Rat pheochromocytoma PC 12 cells were equally distributed with phenol red free Dulbecco's modified Eagle's red medium (DMEM) (Sigma Life Science, USA) containing 10% fetal bovine serum (FBS) in 24-well plate. Cells were pretreated separately with BLPRE and positive control Neostigmin for 1 h. Thereafter, cells were induced with 1 µg/mL of β-amyloid peptide (Calbiochem, USA) for 24 h at 37° C. After 24 h, cells were collected and washed twice with 1×PBS by centrifugation at 1200 rpm for 5 min at 4° C. The cell extracts were prepared in solubilization buffer and the cell lysates were analyzed for acetylcholine esterase (AChE) activity. The BsLPRE showed 25.3% inhibition at 100 ng/mL concentration, where as Neostigmin showed 49.1% inhibition at 20 ng/mL as summarized in Table 4.

Figure 3:
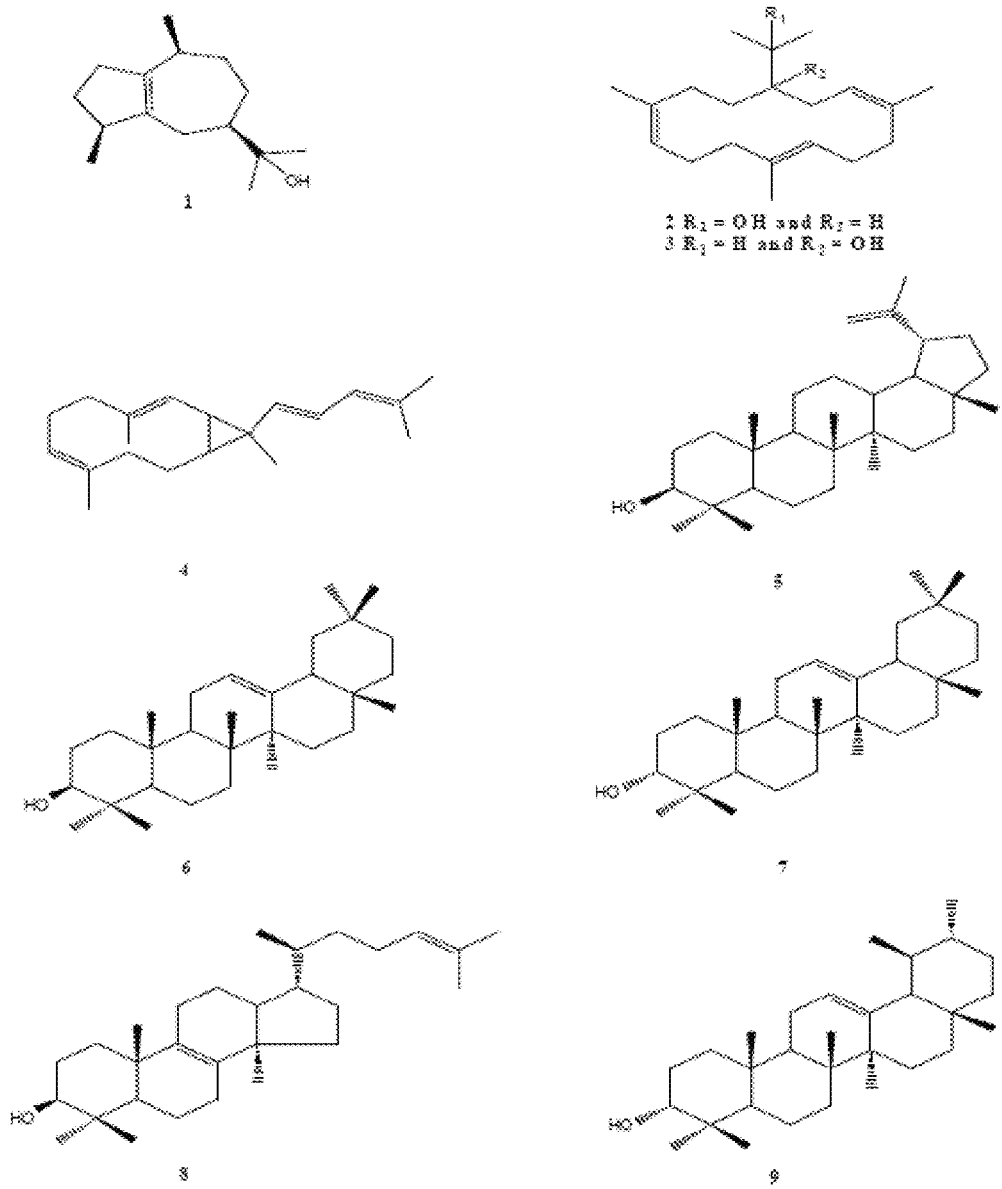
FIG. 3 shows structural formulae I-9 representing prominent compounds of *Boswellia serrata* low polar gum resin extract (BsLPRE).

In order to understand the chemical composition of BsLPRE, separation of BsLPRE was carried out using column chromatography and high performance liquid chromatography (HPLC), and several diterpenoid and triterpenoid compounds were isolated. The structures of the compounds were rigorously characterized using $^1$H NMR, $^{13}$C NMR, DEPT, HSQC and HMBC, Mass spectral data. The compounds so obtained and identified are guiol (1), nephthenol (2), serratol (3), diterpene X (4), lupeol (5), olean-12-ene-3β-ol (6), olean-12-ene-3α-ol (7), lanosta-8, 24-diene-3α-ol (8) and urs-12-ene-3α-ol (9) as depicted in FIG. 3. The fraction, *Boswellia serrata* low polar gum resin extract (BsLPRE) was then standardized to three or more of the phytochemical marker compounds selected from 1 to 9. The typical results obtained are summarized in the Table 1 and a typical chromatogram depicting the profile of BsLPRE is presented in FIG. 4. However, compositions of BsLPRE or any other *Boswellia* low polar gum resin extract composition (BLPRE) obtained from any other species may vary based on several factors such as *Boswellia* species used, age of the plant, season of collection of gum resin, geographic location and manufacturing process employed.

The foregoing results manifest that BsLPRE is a novel composition comprising unique combination of sesquiterpenoids, diterpenoids and triterpenoids and other phytochemical(s). A compound tentatively identified as diterpene X (4) and compounds guiol (1), nepthenol (2) and Lanosta-8,24-diene-3α-ol (8) are not known to be metabolites of *Boswellia serrata* gum resin.

The low polar gum resin extract of these as well as other *Boswellia* species comprise a composition having some similarity to that of *Boswellia serrata*. However, the low polar gum resin extract of *Boswellia carterii* (BcLPRE) has shown biological activity and synergistic effect very similar to that exhibited by BsLPRE as summarized in the following in vitro and in vivo studies. The experimental studies are discussed in the examples.

The acetylcholinesterase inhibitory of different boswellic acids was also evaluated in both enzyme based assay and cell based assay and the inhibitory activities are summarized in Tables 3 and 5.

Oxidative stress induced increased ROS is critical for neuronal damage, which is a serious complication with regard to brain health. Interestingly, the low polar gum resin extract of *Boswellia serrata* (BsLPRE) showed potent inhibition of reactive oxygen species (ROS) generation in RAW 264.7 mouse macrophages (Table 6). In addition, BsLPRE also showed protection from oxidative stress induced cytotoxic damage of human neuroblastoma cells. In a cell based assay, oxidative stress induced by $H_2O_2$ showed potent cytotoxic effect on the proliferation of IMR32 human neuroblastoma cells. However, the treatment with BsLPRE significantly attenuates the proliferation index of IMR32 human neuroblastoma cells back to the normal level (Table 7). Hence the observations confirm that the low polar gum resin extract (BLPRE) offers protection from neuronal damage and support improving brain health.

Figure 5:
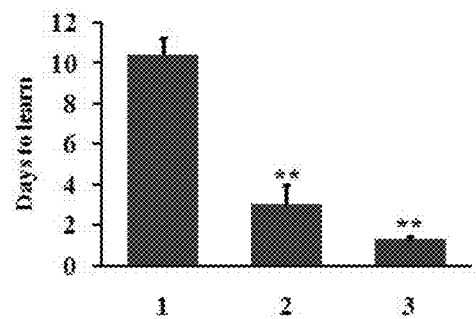
FIGS. 5A, 5B, and 5C show bar diagrammatic representation of number of days required for learning, latency in finding feed and number of wrong entries respectively obtained during learning phase. The bars 1 to 3 represents vehicle treated control, BsLPRE (250 mg/kg) and piracetam (150 mg/kg) respectively. Each bar represent mean±SE, n=8, *p<0.05 and **p<0.01.
Figure 5:
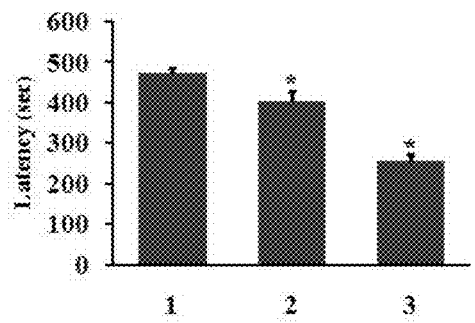
Figure 5:
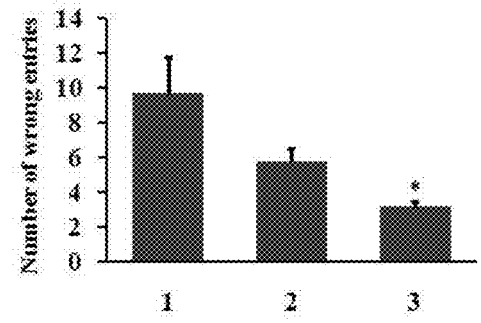
Figure 6:
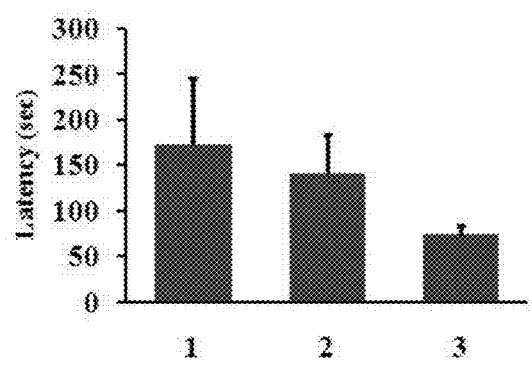
FIGS. 6A and 6B show bar diagrammatic representation of latency in finding feed and number of wrong entries respectively obtained during memory retention phase. The bars 1 to 3 represents vehicle treated control, BsLPRE (250 mg/kg) and piracetam (150 mg/kg) respectively. Each bar represent mean±SE, n=8.
Figure 6:
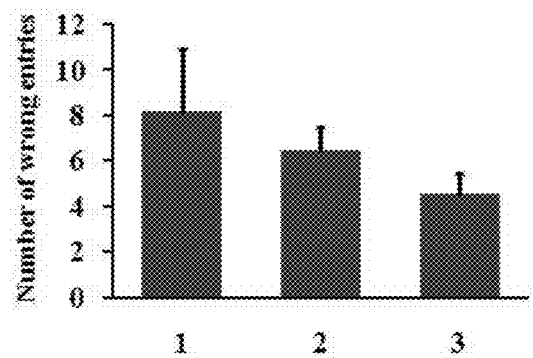

The in vivo efficacy of BsLPRE on learning and memory improvement was proven in rats using elevated radial arm maze (RAM) method. Oral administration of BsLPRE (250 mg/kg) significantly (P<0.01) decreased the number of days required to make the rats learned as per set criteria and significantly (P<0.05) decreased the time taken to find the food by the learned rats in the elevated RAM model. The positive control Piracetin (150 mg/kg) also showed significant improvement in spatial learning like reduction in latency and Number of wrong entries, when compared with the control group and the results are as stated below (FIG. 5A to 5C). The test product BsLPRE also significantly improves cognition and memory retention (FIGS. 6A and 6B). These results confirm the efficacy shown by BsLPRE in vitro and suggest that the use of BsLPRE improves spatial learning and memory retention. According to these findings, BsLPRE is a promising candidate for facilitation of learning and memory.

Synergistic Compositions Comprising *Boswellia* Extracts:

Cell based and enzyme based in vitro anti-acetylcholinesterase studies were conducted on a broad array of *Boswellia* extracts standardized to boswellic acids and *Boswellia serrata* low polar gum resin extract (BsLPRE), in addition to other herbal extracts. The individual extracts and different combination of these extracts were tested for their efficacy to inhibit acetylcholinesterase enzyme. It was found surprisingly that a composition (composition-1) comprising a combination of 1) a *Boswellia serrata* extract containing 85% total boswellic acids (BSE85%) and 2) a *Boswellia serrata* low polar gum resin extract (BsLPRE) showed potent inhibition of acetylcholinesterase (AChE).

Hence, the foregoing shows that BOIL, BVOIL and BLPRE alone as well as in combination with Boswellic acid(s)/*Boswellia* extract(s) or fractions(s) containing boswellic acid(s)/extracts standardized to boswellic acids/one or more Nootropic agents are potent inhibitors of acetylcholinesterase and as such can be used for the prevention, control and treatment of cognitive disorders and improving memory and alleviating disease conditions related to cognition and memory deficits.

Pure boswellic acids and commercially available *Boswellia serrata* extract standardized to 85% boswellic acids have been used to demonstrate the subject matter disclosed herein. However, any *Boswellia serrata* standardized to 40%-100% total boswellic acids by titrimetric method of analysis or standardized to 30%-100% total boswellic acids by HPLC method of analysis can also be used.

Similarly, a composition (composition-34) containing low polar gum resin extract (BLPRE) in combination with α-mangostin offers better protection from neuronal damage (Table 6) and hence can improve brain health. In addition, composition-34 also showed better protection from oxidative stress induced cytotoxic damage of human neuroblastoma cells in a cell based assay (Table 7). This result further confirms the potential role of the composition containing BsLPRE in the improvement of brain health.

Different Embodiments Disclosed Herein are as Outlined Below:

In the primary aspect, the disclosure provides non-acidic *Boswellia* low polar gum resin extract (BLPRE) fraction, *Boswellia* volatile oil (BVOIL) fraction and *Boswellia* oil fraction (BOIL) comprising BLPRE and BVOIL for improving mental condition/brain health, treating impaired memory and alleviating memory and cognition related disorders and other associated diseases in warm blooded animals.

In the other primary aspect the disclosure provides compositions comprising at least one fraction selected from *Boswellia* oil (BOIL), *Boswellia* volatile oil (BVOIL) and *Boswellia* low polar gum resin extract (BLPRE) in combination with one or more biological agents or Nootropic agents for improving mental condition/brain health, treating impaired memory and alleviating memory and cognition related disorders and other associated diseases in warm blooded animal.

In another embodiment the disclosure provides, composition comprising at least one *Boswellia* derived non-acidic extract/fraction selected from *Boswellia* low polar gum resin extract fraction (BLPRE), *Boswellia* volatile oil fraction (BVOIL) and non-acidic *Boswellia* oil fraction (BOIL) in combination with at least one component selected from biological agents, phytochemicals, vitamins, amino acids, minerals; pharmaceutically or dietetically acceptable excipients, vehicles, carriers and diluents or mixtures thereof for improving mental condition/brain health; enhancing brain functions such as cognition, memory, learning, communication; for treating impaired memory, and for preventing, control or treating memory and cognition related disorders/diseases.

In another embodiment the disclosure provides methods for improving brain health and brain functions such as cognition, memory, learning, communication or treating impaired memory in a subject or warm blooded animal in need thereof, wherein the method comprises supplementing the said subject or warm blooded animal with an effective dose of *Boswellia* derived non-acidic extract/fraction or their composition(s).

In another embodiment the disclosure provides methods for preventing, control or treating memory and cognition related disorders/diseases in a subject or warm blooded animal in need thereof, wherein the method comprises supplementing the said subject or warm blooded animal with an effective dose of *Boswellia* derived non-acidic extract/fraction or their composition(s).

In another embodiment the disclosure provides methods of preventing, control or treating memory and cognition related disorders/diseases, wherein memory and cognition related disorders/diseases include but not limited to senile dementia, multi-infarct dementia, dyslexia, aphasia, organic brain syndrome, myasthenia gravis, vascular dementia, mild cognitive impairment (MCI), Attention-deficient Hyperactivity Disorder (ADHD), Lewy body dementia, Wernicke-Korsakoff-syndrome, Alzheimer's, Parkinson's disease, hypoxia, anoxia, cerebrovascular insufficiency, epilepsy, myoclonus and hypocholinergic dysfunctions, memory impairment disorders and neurodegenerative disorders.

In another aspect, the disclosure provides *Boswellia* low polar gum resin extract (BLPRE) fraction, *Boswellia* volatile oil (BVOIL) fraction and *Boswellia* oil (BOIL) fraction comprising BLPRE and BVOIL individually or their composition(s) comprising useful for the prevention, control and treatment of brain related diseases comprising Attention-deficit Hyperactivity Disorder (ADHD) and memory deficits or to enhance brain functions such as cognition, memory, learning and communication Importantly, the said fractions and compositions of the present disclosure help in making the brain healthy.

In another aspect, the disclosure provides compositions comprising at least one component selected from *Boswellia* low polar gum resin extract fraction (BLPRE), *Boswellia* volatile oil fraction (BVOIL) and non-acidic *Boswellia* oil fraction (BOIL) in combination with at least one pharmaceutically/dietetically acceptable excipients/diluents, further optionally comprising one or more agents selected from natural antioxidants, anti-inflammatory agents and immune modulators.

In another embodiment the disclosure provides the composition comprising at least one *Boswellia* derived non-acidic extract/fraction in combination with at least one pharmaceutically/dietetically acceptable excipients/diluents, wherein said pharmaceutically or dietetically acceptable excipients, carriers, vehicles and diluents include but not limited to glucose, fructose, sucrose, maltose, lactose, yellow dextrin, white dextrin, silicon dioxide, microcrystalline cellulose powder, calcium stearate, magnesium stearate, sorbitol, stevioside, corn syrup, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, nicotinamide, calcium pantothenate, calcium salts, pigments, flavors, preservatives, distilled water, saline, aqueous glucose solution, alcohol, propylene glycol and polyethylene glycol, various animal and vegetable oils, white soft paraffin, paraffin and wax.

In another aspect, the disclosure provides *Boswellia* non acidic extracts/fractions selected from *Boswellia* low polar gum resin extract fraction (BLPRE), *Boswellia* volatile oil fraction (BVOIL) and non-acidic *Boswellia* oil fraction (BOIL) and their compositions to prevent, control and treat brain related diseases/disorders which include but not limited to senile dementia, multi-infarct dementia, dyslexia, aphasia, organic brain syndrome, myasthenia gravis, vascular dementia, mild cognitive impairment (MCI), Lewy body dementia, Wemicke-Korsakoff-syndrome, Alzheimer's, Parkinson's disease, Attention-deficit Hyperactivity Disorder (ADHD), hypoxia, anoxia, cerebrovascular insufficiency, epilepsy, myoclonus and hypocholinergic dysfunctions, memory impairment disorders and neurodegenerative disorders In another aspect, the disclosure provides *Boswellia* derived non-acidic extract/fraction or their composition(s) for improving mental condition/brain health by slowing down memory deterioration, functional loss, by inhibiting beta-amyloid plaque deposition, by controlling blood pressure and blood circulation in the brain.

In another aspect, the Nootropic agent(s) used for making the composition comprise one or more agent(s) selected from smart drugs, memory enhancers and cognitive enhancers; dietary supplements, herbal ingredients, nutraceuticals, functional ingredients and functional foods that improve mental functions such as cognition, memory, intelligence, motivation, attention and concentration.

In another aspect, the Nootropic agents can be selected from one or more components selected from the extract(s)/fraction(s)/phytochemicals derived from herbs including but not limited to *Bacopa* species, *Curcuma* species or *Rosmarinus* species.

In another aspect, the herbal ingredients that can be used for preparing compositions are selected from including but not limited to *Boswellia serrata*, *Boswellia carterii*, *Bacopa monniera*, *Curcuma longa*, *Withania somnifera*, *Rosmarinus officinalis*, *Garcinia mangostana*, α-mangostin, *Annona squamosa* and *Sphaeranthus indicus*.

In another aspect of the disclosure, the Nootropic agents can be selected from extract(s)/fraction(s)/phytochemicals, extracts/fractions enriched in one or more phytochemicals selected from including but not limited to *Bacopa monnieri*, *Withania somnifera*, *Emblica officinalis*, *Centella asiatica*; extract or fraction enriched in one or more phytochemicals selected from including but not limited to Bacoside A3, Bacopaside II, Jujubogenin isomer of bacopasaponin C, Bacopasaponin C, Bacopaside I, Bacosine, Apigenin, Luteolin and Sitosterol-D-glucoside, curcumin, demethoxycurcumin, bisdemethoxycurcumin, monodemethylcurcumin, bisdemethylcurcumin, tetrahydrocurcumin, tetrahydrodemethoxycurcumin, tetrahydrobisdemethoxycurcumin and ar-turmerone, carnosic acid, rosmarinic acid, camphor, caffeic acid, ursolic acid, betulinic acid, rosmaridiphenol, rosmanol and their salts thereof.

In yet another aspect, the disclosure provides compositions comprising therapeutically effective combination of *Boswellia* oil (BOIL/*Boswellia* volatile oil BVOIL)/*Boswellia* low polar gum resin extract (BLPRE) in combination with at least one *Boswellia* derived component selected from the extract(s), fraction(s) enriched with one or more boswellic acids/pure boswellic acid compounds or Nootropic agents for improving memory, impaired memory and alleviating memory and cognition related disorders and other associated diseases.

In another aspect, the disclosure provides compositions for the cognition enhancement achieved through one or more biological actions comprising inhibition of Acetylcholinesterase, increase in Butyrylcholinesterase and inhibition of (3-amyloid aggregation.

In yet another aspect, the disclosure further provides compositions comprising *Boswellia* oil (BOIL)/*Boswellia* volatile oil (BVOIL)/*Boswellia* low polar gum resin extract (BLPRE) and at least one component, derived from gum resin of *Boswellia* species, which include but not limited to α-boswellic acid, 3-boswellic acid, 3-O-acetyl-α-boswellic acid, 3-O-acetyl-β-boswellic acid, 3-O-acetyl-11-keto-α-boswellic acid and 3-O-acetyl-11-keto-β-boswellic acid or mixtures thereof for improving memory, impaired memory and alleviating memory and cognition related disorders and other associated diseases.

In yet another important aspect, the disclosure further provides compositions comprising *Boswellia serrata* low polar gum resin extract (BsLPRE) or BsVOIL or BsOIL and at least one *Boswellia* derived component selected from the extracts or fractions enriched in or standardized to one or more compounds derived from the gum resin of *Boswellia* which include but not limited to α-boswellic acid, β-boswellic acid, 3-acetyl-α-boswellic acid, 3-acetyl-β-boswellic acid, 3-acetyl-11-keto-α-boswellic acid and 3-acetyl-11-keto-β-boswellic acid or mixtures thereof for improving memory, improving impaired memory and alleviating memory and cognition related disorders and other associated diseases.

In another aspect, the disclosure further provides compositions comprising *Boswellia serrata* low polar gum resin extract (BsLPRE) or BsVOIL or BsOIL and a *Boswellia serrata* extract standardized to 30-100% total boswellic acids by titrimetric method of analysis or 20-100% total boswellic acids by HPLC method of analysis.

In preferred aspect, the disclosure further provides compositions comprising *Boswellia serrata* low polar gum resin extract (BsLPRE) or BsVOIL or BsOIL and *Boswellia* serrata extract standardized to 85% total boswellic acids by titrimetric method of analysis or 65% total boswellic acids by titrimetric method of analysis.

In another preferred aspect, the disclosure provides compositions comprising *Boswellia* serrata low polar gum resin extract (BsLPRE) or BsVOIL or BsOIL and *Boswellia* serrata extract selectively enriched in AKBA concentration varying from 3-99% by HPLC method of analysis.

In other preferred embodiment, the disclosure further provides a process for producing the *Boswellia* low polar gum resin extract (BLPRE), which include extraction of the gum resin of *Boswellia* species with a water immiscible organic solvent followed by washing the organic solvent extract with an aqueous alkali solution such as aqueous potassium hydroxide, followed by water and brine, and then finally evaporating the organic layer under vacuum to obtain an oil, followed by removing the volatile compounds under high vacuum and temperature to obtain BLPRE. The water immiscible organic solvent can be selected from hexane, chloroform, dichloromethane, ethyl acetate, methyl isobutyl ketone or any other water immiscible solvent or mixtures thereof.

The process for producing the *Boswellia serrata* low polar gum resin extract (BsLPRE) is variable and the alternative process for example comprise, extracting the gum resin with alcohol or hydroalcohol, and then evaporating the organic solvent to optimum concentration of total solids and then adjusting the solution to pH to 9-11, followed by repeatedly extracting the solution with a low polar organic solvent and then evaporating the organic solvent followed by removing the volatiles under vacuum at high temperature to obtain BsLPRE.

In a further embodiment, the *Boswellia serrata* intact oil can also be used in place of BsLPRE for improving memory, impaired memory and alleviating memory and cognition related disorders and for making the compositions of the present disclosure.

The water immiscible organic solvent in the above process can be selected from the solvents but not limited hexane, chloroform, dichloromethane, ethyl acetate, methylisobutylketone, tert-butanol or any other water immiscible solvent.

The *Boswellia serrate* extract standardized to 30-100% total boswellic acids by a titrimetric method of analysis or 20-100% total boswellic acids by HPLC method of analysis can be prepared from the gum resin using a known procedure or obtained from a group of commercially available *Boswellia serrata* extracts standardized to boswellic acids.

In another aspect of the disclosure, the non acidic extracts *Boswellia* oil (BOIL), *Boswellia* volatile oil (BVOIL), *Boswellia* low polar gum resin extract (BLPRE) used for the demonstration of the disclosure can be obtained from the *Boswellia* species selected from *Boswellia serrata, Boswellia carterii, Boswellia papyrifera, Boswellia ameero, Boswellia bullata, Boswellia dalzielii, Boswellia dioscorides, Boswellia elongata, Boswellia frereana, Boswellia nana, Boswellia neglecta, Boswellia ogadensis, Boswellia pirottae, Boswellia popoviana, Boswellia rivae, Boswellia sacra* and *Boswellia socotrana*.

In another aspect of the disclosure one or more of the *Curcuma* species that can be used for making the compositions of the present disclosure can be selected from *Curcuma longa, Curcuma aromatica, Curcuma domestica, Curcuma aeruginosa, Curcuma albicoma, Curcuma albiflora, Curcuma alismatifolia, Curcuma angustifolia, Curcuma elata, Curcuma ferruginea, Curcuma flaviflora, Curcuma yunnanensis* and *Curcuma zedoaria*.

In yet another aspect of the present disclosure, BOIL, BVOIL or BLPRE alone or in combination with one or more *Boswellia* derived extracts selectively enriched in boswellic acids/commercially available boswellic extract(s) standardized to 50-100% total boswellic acids/*Boswellia serrata* extracts wherein AKBA concentration varies from 3-99% HPLC method of analysis and optionally contains one or more of pharmaceutically/nutraceutically/dietically acceptable excipient(s), diluents, salt(s), additive(s), natural antioxidants or natural anti-inflammatory agents.

In another aspect, the disclosure provides the usage of BOIL, BVOIL or BLPRE alone or their compositions as it is or in comminuted form and/or in unmodified form as granules or powder or paste or the active ingredients are formulated into a solid, semi-solid or liquid dosage form by adding a conventional biologically or pharmaceutically acceptable salt(s) or additive(s) or excipient(s).

In yet another aspect, the disclosure provides use of therapeutically effective amount of BOIL, BVOIL or BLPRE alone or their compositions with one or more biological agents or Nootropic agents for administration in a specific dosage form such as orally, topically, transdermally, parenterally or in the form of a kit to a subject or patient in need thereof. Specific dosage form for formulation of the compositions of the present disclosure include but not limited to oral agents such as tablets, soft capsule, hard capsule, soft gel capsules, pills, granules, powders, emulsions, suspensions, syrups, pellets, food, beverages, concentrated shots, drops and the like; parenteral agents such as injections, intravenous drip and the like; suppositories; transdermal agents such as patches, topical creams and gel; ophthalmic agents and nasal agents.

In another aspect, the present disclosure provides compositions containing at least one extract/fraction selected from BOIL, BVOIL or BLPRE in combination with one or more functional ingredient(s) comprising herbal ingredients, dietary supplements, antioxidants, vitamins, minerals, amino acids, fatty acids, essential oils, fish oils, enzymes, glucosamine, Chondroitin and probiotics or their salts or mixtures thereof derived from plants or animals or microorganisms or chemical synthesis or semi-synthesis.

In a further aspect, the present disclosure provides BOIL, BVOIL or BLPRE alone or their compositions further optionally combined with effective amounts of one or more pharmaceutical/nutraceutical/dietically acceptable agents including but not limited to antioxidant(s), adaptogen(s), anti-acetylcholinesterase agent(s), anti-inflammatory agent(s), anti-diabetic agent(s), antiobese agent(s), antiatherosclerotic agent(s), bio-protectants and/or bio-availability enhancer(s) and trace metals.

The examples of the biologically/pharmaceutically acceptable carriers employed in the present disclosure include, but are not limited to, surfactants, excipients, binders, diluents, disintegrators, lubricants, preservatives, stabilizers, buffers and suspensions.

In alternative aspect of the disclosure, the BOIL, BVOIL or BLPRE alone or their compositions can be optionally delivered in the form of controlled release dosage forms; and by using techniques including nanotechnology, microencapsulation, colloidal carrier systems and other drug delivery systems. The said formulation can be designed for once a daily administration or multiple administrations per day.

In accordance to the present disclosure, the BOIL, BVOIL or BLPRE alone or their compositions can also be formulated into or added to existing or new food and beverage form(s) and animal feeds as a healthy food or beverage or feed.

In accordance to the present disclosure, the BOIL, BVOIL or BLPRE alone or their compositions can also be formulated into or added to existing or new food and beverage form(s) and animal feeds as a healthy food or beverage or feed for prevention, control and treatment of brain related diseases/disorders.

In yet another embodiment, the composition can comprise 10%-99% by the weight of *Boswellia serrata* derived component selected from the extract(s) and fraction(s) enriched with one or more boswellic acids, pure boswellic acid compounds and mixtures thereof and 90%-10% by weight of *Boswellia serrata* low polar gum resin extract BsLPRE or BsVOIL or BsOIL.

C. Use of *Boswellia* Non-Acidic Extracts as Bio-Enhancing Agents

During the search for bioenhancing agents, it was found that non-acidic *Boswellia* low polar gum resin extract fraction (BLPRE), *Boswellia* volatile oil fraction (BVOIL) or *Boswellia* oil fraction (BOIL) comprising BLPRE and BVOIL enhance the bioavailability of bioactive agents. The compositions LI13108F containing *Boswellia serrata* low polar gum resin extract (BsLPRE; LI13115) and *Boswellia serrata* extract selectively enriched to 30% 3-O_acetyl-11-keto-β-boswellic acid (AKBA) and LI13119F containing *Boswellia serrata* volatile oil fraction (BsVOIL) and *Boswellia serrata* extract selectively enriched to 30% 3-O_acetyl-11-keto-β-boswellic acid (AKBA) were supplemented to Albino Wistar rats. The control group of animals was supplemented with *Boswellia* serrata extract selectively enriched to 30% AKBA. Blood samples were collected from all animals prior to oral administration of test products and at 0.5, 1, 2, 4, 8 and 12 hrs after oral administration. The comparative oral bioavailability of AKBA from these *Boswellia* products was evaluated by measuring the serum AKBA concentration for each test animal using LC-MS.

Figure 7:
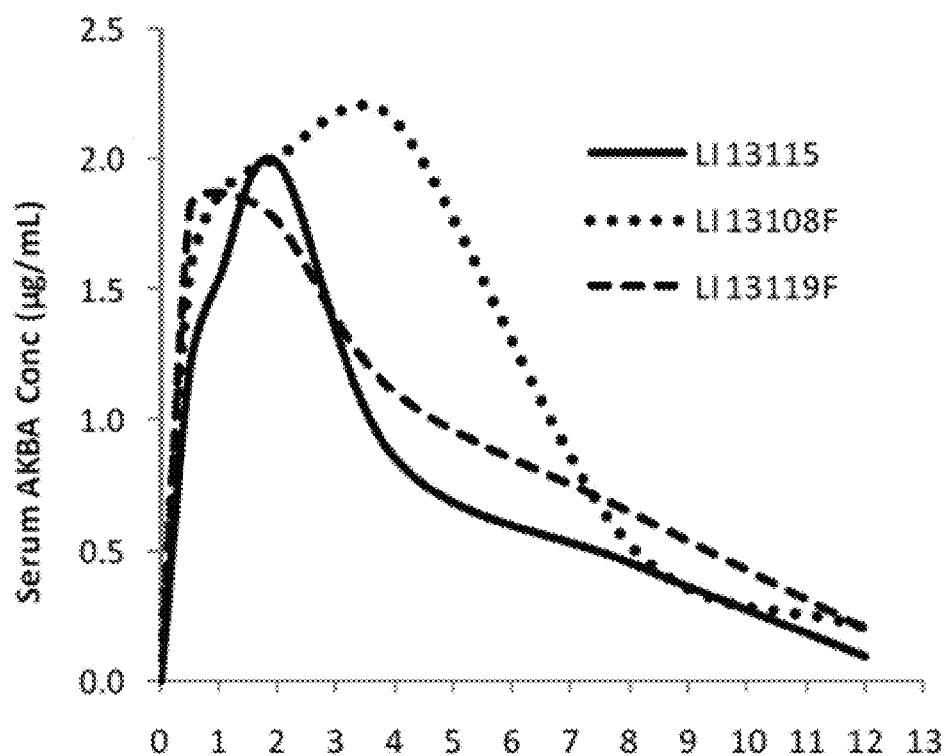
FIG. 7 shows a plot of serum concentration of AKBA after oral administration of the composition LI13108F containing *Boswellia serrata* low polar gum resin extract (BsLPRE) and *Boswellia serrata* extract selectively enriched to 30% 3-O-acetyl-11-keto-β-boswellic acid (AKBA) and composition LI13119F containing *Boswellia serrata* volatile oil fraction (BsVOIL) and *Boswellia serrata* extract selectively enriched to 30% 3-O-acetyl-11-keto-β-boswellic acid (AKBA) to albino rats at doses equivalent to 30 mg/kg of AKBA.

Surprisingly, both the compositions LI 13108F and LI 13119F showed better oral bioavailability with AUCs 14.08 and 11.23 respectively compared to AUC 9.825 shown by individual ingredient *Boswellia serrata* extract containing 30% AKBA (LI 13115). The bioavailability (in terms of AUC) of LI 13108F is 43.33% more than LI 13115. The bioavailability of LI 13119F is 14.33% more than that of LI 13115. The study details are summarized in example-5 and depicted in FIG. 7.

To exert optimal therapeutic efficacy, an active substance should reach systemic circulation and site of its action in an effective concentration during the desired period. Improving bioavailability and reducing dosage frequency without losing therapeutic benefit is crucial in achieving therapeutic efficacy and patient compliance in chronic treatment regimes. The compositions disclosed herein achieve this objective by enhancing the oral bioavailability of AKBA in compositions containing BsLPRE.

Figure 8:
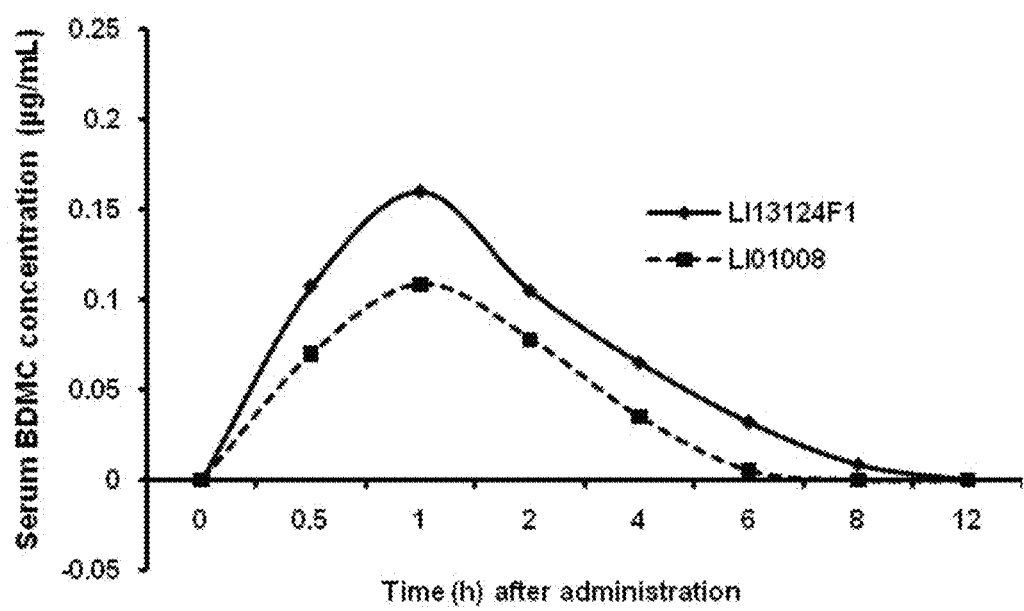
FIG. 8 represents a plot of serum concentration of Bisdemethylcurcumin (LI01008) after oral administration of composition (LI13124F1) containing Bisdemethylcurcumin and *Boswellia serrata* low polar gum resin extract (BsLPRE) in 2:1 ratio at concentration of 450 mg/kg or Bisdemethylcurcumin (LI01008) alone at 300 mg/kg body weight.

The bioavailability enhancing effect of BsLPRE was further confirmed by evaluating the composition LI13124F1 containing BsLPRE and a novel curcumin compound called bisdemethylcurcumin (LI01008) in comparison with LI01008 alone in Alibino Wistar rats. Bisdemethylcurcumin is a potent curcuminoid, far superior to other naturally occurring curcuminoids with respect to antioxidant and other biological activities commonly exhibited curcumins. The composition LI13124F1 showed better bioavailability of LI01008 in serum samples compared to the animals supplemented with LI01008 alone. The serum samples of animals supplemented with LI13124F1 showed 75% better bioavailability compared to the serum samples of the animals supplemented with LI01008 alone. The experimental studies are discussed in example-6 and depicted in FIG. 8.

The foregoing thus suggest that the non-acidic *Boswellia* low polar gum resin extract fraction (BLPRE), *Boswellia* volatile oil fraction (BVOIL) or *Boswellia* oil fraction (BOIL) comprising BLPRE and BVOIL enhance the bioavailability of bioactive agents. These bio-enhancing agents thus can be useful to improve the efficacy and reduce the dose of bioactive agents.

In an important aspect, the current disclosure provides bioenhancing agents selected from intact *Boswellia* oil (BOIL), *Boswellia* volatile oil (BVOIL) and *Boswellia* low polar gum resin extract (BLPRE) obtained from *Boswellia* gum resin of *Boswellia* species for increasing the bioavailability of biological agents.

In an important aspect, the current disclosure provides compositions comprising one or more ingredients selected from intact *Boswellia* oil (BOIL), *Boswellia* volatile oil (BVOIL) and *Boswellia* low polar gum resin extract (BLPRE) obtained from *Boswellia* gum resin of *Boswellia* species in combination with a biological agent for increasing the bioavailability of biological agent.

In another aspect, the current disclosure provides *Boswellia* derived bioenhancing agents for improving the bioavailability and/or bio-efficacy of nutraceuticals or dietary supplements is also relevant to animal health besides being important for humans.

In another aspect the current disclosure provides *Boswellia* derived bioenhancing agents for increasing the bioavailability of one or more biological ingredient(s) or functional ingredient(s).

In another aspect the current disclosure provides *Boswellia* derived bioenhancing agents for increasing the bioavailability of one or more *Boswellia* derived components.

In another aspect the current disclosure provides *Boswellia* derived bioenhancing agents for increasing the bioavailability of one or more *Curcuma longa* derived components.

In another aspect the current disclosure provides the method of using *Boswellia* derived bioenhancing agents for enhancing the bioavailability of biological agents.

In another aspect, the current disclosure provides bioenhancing agents, which function through one or more of the mechanisms comprising increasing the bioavailability, enhancing the serum concentration, improving gastrointestinal absorption, improving systemic utilization and improving cross over through certain biological barriers like respiratory lining, urinary lining, blood brain barrier and skin.

In another aspect, the current disclosure provides bio-enhancing agents *Boswellia* oil (BOIL), *Boswellia* volatile oil (BVOIL) and *Boswellia* low polar gum resin extract (BLPRE) derived from the gum resin of *Boswellia* where in the gum resin can be obtained from one or more of the *Boswellia* species selected from *Boswellia serrata, Boswellia carterii* and *Boswellia papyrifera*.

In another aspect the current disclosure provides compositions for bioenhancing the activity of biological agents in warm blooded animals in need thereof.

In another aspect the current disclosure provides compositions comprising *Boswellia* oil (BOIL), *Boswellia* volatile oil (BVOIL) and *Boswellia* low polar gum resin extract (BLPRE) for enhancing the bioavailability of nutraceutical or dietary ingredients in warm blooded animals in need thereof.

The nutraceutically/dietetically acceptable agents comprise one or more ingredients selected from phytochemicals, Nootropic agents, anti obese agents, anti-inflammatory agents, anti cholesterol agents, anti arthritic agents, anti diabetic agents, antimicrobial agents, anti fungal agents, anti cancer agents, anti hypertensive agents, analgesic agents, anti platelet aggregation agents, anti atherosclerotic agents, antioxidants, anti thrombotic agents, antibiotic agents, anti malarial agents, anti osteoporotic agents, probiotics agents, anti fungal agents, immune potentiating agents, anti viral agents, anti histamines, muscle relaxants, anti depressants, hypnotic agents and their salts thereof.

In another aspect the current disclosure provides composition(s) for increasing the bioavailability of one or more biological ingredient(s) selected from biologically active ingredient(s), functional ingredient(s), herbal ingredient(s), dietary supplement(s), nutrient(s), anti-oxidant(s), vitamin(s), mineral(s), amino acid(s), and oil(s) their mixtures obtained from plant(s)/animal(s)/microorganism(s)/synthesis/semi-synthesis.

The functional ingredient(s) comprise one or more ingredients selected from nutrients, dietary supplements, nutritional ingredients, herbal ingredients, phytochemicals, animal proteins, glucosamine, chondroitin, plant proteins, fruit extracts, animal extracts, algae extracts, probiotics and their salts thereof.

The herbal ingredient(s) comprise one or more ingredients selected from extracts/fractions/phytochemicals and their salts derived from *Withania somnifera, Bacopa monniera, Boswellia* species, *Curcuma* species, *Centella asiatica, Sphaeranthus indicus, Annona squamosa, Holoptelia integrifolia, Piper betel, Dolichos biflorus, Moringa oleifera* and *Murraya koenigii*.

The anti-oxidant(s) comprise one or more ingredients selected from vitamin A, vitamin C, vitamin E, alpha-carotene, trans-beta-carotene, betacryptoxanthin, lycopene, lutein/zeaxanthin, pine bark bioflavanols complex, germanium, selenium and zinc. The vitamin(s) comprise one or more water soluble vitamins selected from vitamin B1 vitamin B2, niacinamide, vitamin B6, vitamin B12, folic acid and vitamin C; fat-soluble vitamins selected from vitamin A, vitamin D, vitamin E and vitamin K.

The mineral(s) comprise one or more minerals selected from calcium, iron, zinc, vanadium, selenium, chromium, iodine, potassium, manganese, copper and magnesium. The amino acid(s) comprise one or more amino acids selected from lysine, isoleucine, leucine, threonine, valine, tryptophan, phenylalanine, methionine, L-selenomethionine and their mixtures thereof.

The oil(s) comprise one or more oils selected from omega-3 fatty acid, flaxseed oil, fish oils, krill oil, essential oils and volatile oils.

The biological activity of *Boswellia* derived compounds/phytochemicals that can be enhanced by bioenhancing agents include extracts of fractions standardized to one or more boswellic acids selected from α-Boswellic acid, β-Boswellic acid, 3-O-acetyl-α-Boswellic acid, 3-O-acetyl-β-Boswellic acid, 3-O-acetyl-11-keto-α-Boswellic acid, 11-keto-β-Boswellic acid and 3-O-acetyl-11-keto-β-Boswellic acid.

In another aspect, the current disclosure provides bio-enhancing agents selected from *Boswellia* oil (BOIL), *Boswellia* volatile oil (BVOIL) and *Boswellia* low polar gum resin extract (BLPRE) derived from the gum resin of *Boswellia* for enhancing the bioavailability of extracts/fractions particularly standardized to 3-O-acetyl-11-keto-β-Boswellic acid (AKBA).

In another aspect, the current disclosure provides *Boswellia* derived agents and compositions for enhancing the bioavailability of the phytochemicals derived from *Boswellia* species including but not limited to boswellic acids selected from α-boswellic acid, β-boswellic acid, 3-acetyl-α-boswellic acid, 3-acetyl-β-boswellic acid, 3-acetyl-11-keto-α-boswellic acid and 3-acetyl-11-keto-β-boswellic acid or mixtures thereof.

The *Boswellia* species that can be used for producing the oil (BOIL) or volatile oil (BVOIL) or low polar gum resin extract (BLPRE) from the gum resin comprise one or more species selected from *Boswellia serrata, Boswellia carterii, Boswellia payrifera. Boswellia ameero, Boswellia bullata, Boswellia dalzielii, Boswellia dioscorides, Boswellia elongata, Boswellia frereana, Boswellia nana, Boswellia neglecta, Boswellia ogadensis, Boswellia pirottae, Boswellia popoviana, Boswellia rivae, Boswellia sacra* and *Boswellia socotrana*.

In another aspect, the current disclosure provides *Boswellia* oil or *Boswellia* volatile oil or *Boswellia* low polar gum resin extract for enhancing the bioavailability of one or more *Curcuma* derived extracts/fractions/components/phytochemicals that can be enhanced by bioenhancing agents include extracts of fractions standardized to selected from curcumin, demethoxycurcumin, bisdemethoxycurcumin, monodemethylcurcumin, bisdemethylcurcumin, tetrahydrocurcumin, tetrahydrodemethoxycurcumin, tetrahydro bisdemethoxycurcumin and ar-turmerone or mixtures thereof.

In another aspect, the current disclosure provides bio-enhancing agents *Boswellia* oil (BOIL), *Boswellia* volatile oil (BVOIL) and *Boswellia* low polar gum resin extract (BLPRE) derived from the gum resin of *Boswellia* for enhancing the bioavailability of extracts/fractions particularly standardized to curcumin or demethoxycurcumin or bisdemethoxycurcumin or mixtures thereof.

In another aspect, the current disclosure provides *Boswellia* derived bioenhancing agents and for enhancing the bioavailability of the one or more phytochemicals derived from *Curcuma* species selected from curcumin, demethoxycurcumin, bisdemethoxycurcumin, monodemethylcurcumin, bisdemethylcurcumin, tetrahydrocurcumin, tetrahydrodemethoxycurcumin, tetrahydro bisdemethoxycurcumin and ar-turmerone or mixtures thereof.

The Curcumin derived components that can be bioenhanced are derived from *Curcuma longa, Curcuma aromatica, Curcuma domestica, Curcuma aeruginosa, Curcuma albicoma, Curcuma albiflora, Curcuma alismatifolia, Curcuma angustifolia, Curcumaelata, Curcuma ferruginea, Curcuma flaviflora, Curcuma yunnanensis* and *Curcuma zedoaria*.

D. Examples

The following examples, which include various embodiments, will serve to illustrate the practice of the disclosed subject matter, and it should be understood that the particulars shown are by way of example and for purpose of illustrative discussion of certain embodiments of the invention; the following examples do not limit the scope of the invention.

Example 1

A Process for Preparation of the Non-Acidic *Boswellia* Extract (BOIL) Comprises g) Procuring the gum resin of one or more of the plant(s) selected from but not limited to *Boswellia serrata* or *Boswellia carterii* or *Boswellia papyrifera* or mixtures thereof,
h) Extraction of the gum resin with a water immiscible organic solvent,
i) Filtering the extract carefully to remove the insoluble resin material,
j) Washing the organic solvent extract repeatedly with an aqueous alkali solution such as aqueous potassium hydroxide,
k) Washing the organic layer with water and brine,
l) Evaporating the organic layer under vacuum and high temperature to obtain the oily residue (BOIL).

Example 2

A Process for Preparation of the Non-Acidic *Boswellia* Volatile Oil Fraction (BVOIL) Comprises a) Procuring the gum resin of one or more of the plant(s) selected from but not limited to *Boswellia serrata* or *Boswellia carterii* or *Boswellia papyrifera* or mixtures thereof, b) Separating the Volatile oil component by either steam distillation or distillation under high vacuum and temperature from the said gum resin to obtain *Boswellia* volatile oil fraction (BVOIL).

Example 3

A Process for Preparation of the Non-Acidic *Boswellia* Low Polar Gum Resin Extract Fraction (BLPRE) Comprises a) Procuring the gum resin of one or more of the plant(s) selected from but not limited to *Boswellia serrata* or *Boswellia carterii* or *Boswellia papyrifera* or mixtures thereof,
b) Extraction of the gum resin with a water immiscible organic solvent,
c) Filtering the extract carefully to remove the insoluble resin material,
d) Washing the organic solvent extract repeatedly with an aqueous alkali solution such as aqueous potassium hydroxide,
e) Washing the organic layer with water and brine,
f) Evaporating the organic layer under vacuum and high temperature to obtain the oily residue (*Boswellia* oil).
g) Taking the said oily residue and removing the volatiles under high vacuum and high temperature to obtain *Boswellia* low polar gum resin extract fraction (BLPRE).

Example 4

Representative Procedure for the Preparation of *Boswellia serrata* Low Polar Gum Resin Extract Fraction (BsLPRE)

The *Boswellia serrata* gum resin (100 g) was dispersed in 600 mL of methyl isobutyl ketone (MIBK) solvent and stirred at room temperature for 60 min. The insoluble gum materials were separated by filtration. The MIBK solution was extracted repeatedly with 2% KOH solution (3×200 mL) to remove the acidic compounds. The MIBK layer was then washed successively with water (400 mL) and brine (200 mL). The MIBK layer was evaporated under reduced pressure at 60-70° C. and the volatile components are removed from the oily residue under high vacuum at 75-110° C. to obtain BsLPRE as a viscous oil (12 g).

Alternatively, the gum resin (250 g) collected from *Boswellia serrata* was extracted with methanol (300 mL×3) and the combined methanol extract was concentrated. The residue (50 g) was dissolved in ethyl acetate (400 mL) and extracted thrice with 1N KOH (3×100 mL). The organic layer was washed with water (2×200 mL) and brine (200 mL) and evaporated to obtain *Boswellia* oil. The volatile compounds were evaporated from the oil under vacuum at high temperature (75-110° C.) to obtain 22 g of BsLPRE.

Figure 4:
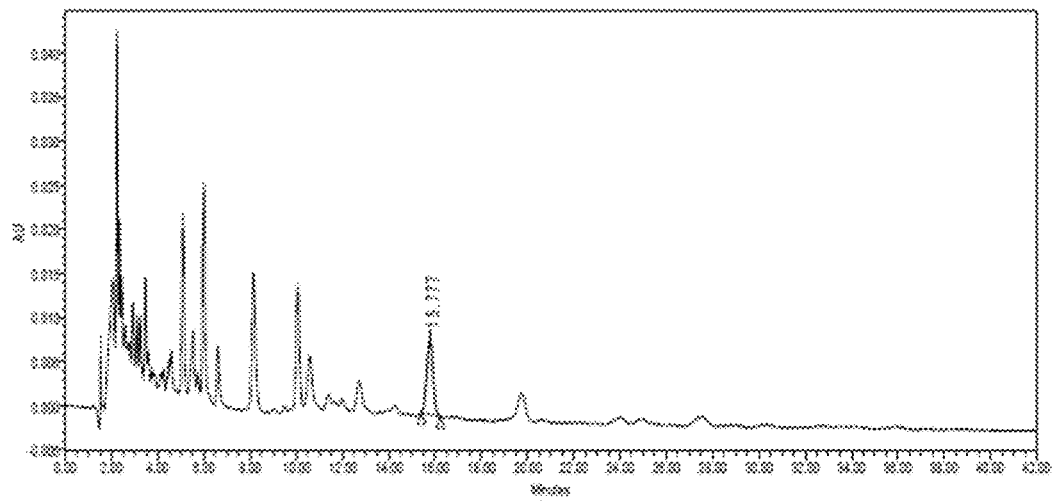
FIG. 4 shows the HPLC chromatogram depicting the phytochemical profile of the *Boswellia serrata* low polar gum resin extract (BsLPRE).
Figure 4:
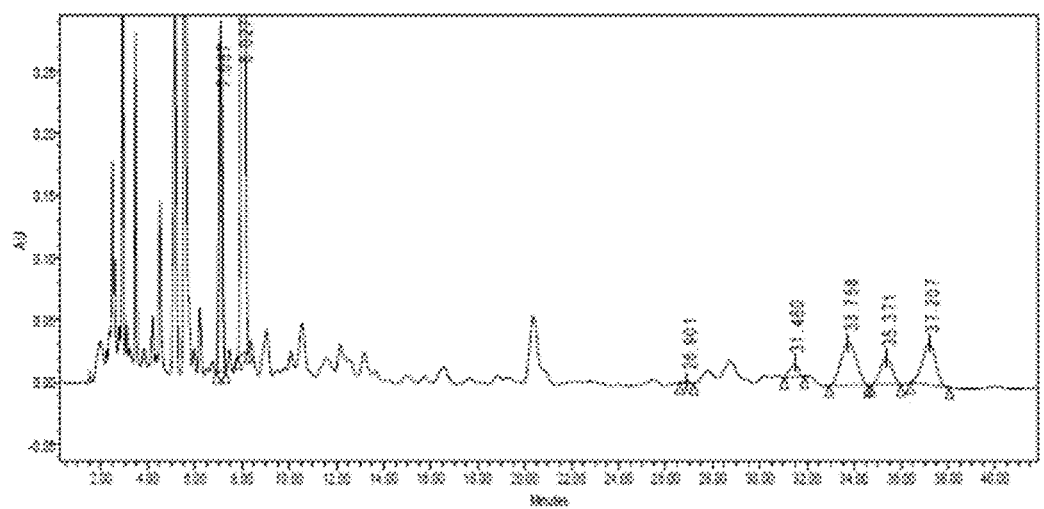

The BsLPRE was subjected to column chromatography over normal silica gel using solvents of increasing polarity starting from hexane to hexane/ethyl acetate mixtures to ethyl acetate. The identical fractions were combined based on TLC and combined fractions were subjected individually to column chromatography over silica gel using mixtures of hexane/ethyl acetate or hexane/acetone as eluents to obtain pure compounds. Some of the impure fractions were further subjected to preparative HPLC using a reversed phase C18 silica column to obtain pure compounds. The structures were established by analyzing the $^1$H NMR, $^{13}$C NMR, DEPT, HSQC and HMBC and mass spectral data and then comparing the data with that of known compounds. Nine of the prominent compounds are identified as guiol (1), nephthenol (2), serratol (3), diterpene X (4), lupeol (5), olean-12-ene-3β-ol (6), olean-12-ene-3α-ol (7), lanosta-8,24-diene-3α-ol (8) and urs-12-ene-3α-ol (9) as depicted in FIG. 3. The pure compounds were then utilized to standardize the *Boswellia serrata* low polar gum resin extract (BsLPRE) using HPLC method. The novel composition of BsLPRE evaluated based on analytical HPLC method along with the retention times ($R_t$) is summarized in Table 1. The HPLC chromatogram for BsLPRE is depicted in FIG. 4.

TABLE 1

Composition of *Boswellia serrata* low polar gum resin extract fraction (BsLPRE)

| S. No | Test substance | $R_t$ in min | Percentage |
|---|---|---|---|
| 1 | Guiol (1) | 4.5 | 0.96 |
| 2 | Nephthenol (2) | 7.087 | 2.01 |
| 3 | Serratol (3) | 8.027 | 13.32 |
| 4 | Diterpene X (4) | 15.777 | 0.12 |
| 5 | Lupeol (5) | 26.901 | 0.06 |
| 6 | Olean-12-ene-3β-ol (6) | 31.460 | 1.29 |
| 7 | Olean-12-ene-3α-ol (7) | 33.718 | 5.36 |
| 8 | Lanosta-8,24-diene-3α-ol (8) | 35.371 | 1.34 |
| 9 | Urs-12-ene-3α-ol (9) | 37.207 | 4.55 |

Example 5

*Boswellia serrata* Extract Standardized to 50-100% Total Boswellic Acids (Titrimetric Method)

*Boswellia serrata* extracts standardized to 85% or 65% total boswellic acids are commercially available. These extracts are standardized using titrimetric method of analysis. These extracts can be prepared using a known procedure. For example, by extracting the gum resin of *Boswellia serrata* using a water immiscible solvent and then selectively extracting the acidic compounds from the organic solvent extract using aqueous alkali solution through phase separation. Finally acidification of the alkali solution to precipitate the boswellic acids followed by vacuum drying to yield *Boswellia* serrata extract enriched to 85% boswellic acids (BE85%). *Boswellia serrata* extracts standardized to a selected concentration of total boswellic acids in the range of 40-100% by titrimetric method of analysis or 30-100% by HPLC method of analysis can be obtained by purification of the gum resin or the extracts or by dilution of higher grade material.

Example 6

Determination of Acetylcholinesterase Inhibitory Activity of BsOIL, BsLPRE, BcLPRE, BsVOIL and Different Boswellic Acid Compound in an In Vitro Enzymatic Assay Acetylcholinesterase activity is measured using the substrate acetylthiocholine iodide, which is converted to thiocholine. The reaction of thiocholine with the chromogenic substrate Dithionitrobenzoic acid (DTNB) leads to the formation of a yellow anion, Nitrobenzoic acid, which absorbs strongly at 412 nm Incubation was done for 10 min.

The AChE assay was performed by the method of Ellman et al., with minor modifications, using acetylthiocholine iodide as a substrate (Lee J. H., et. al. *Arch Pharm Res* 2004, 27(1): 53-56). Ellmans reaction mixture contains 0.5 mM acetylthiocholine iodide and 1 mM 5,5'-dithio-bis-(2-nitrobenzoic acid) in a 50 mM sodium phosphate buffer (pH 8.0). The assay mixture contained 50 µl of 50 mM phosphate buffer at pH–8.0, 30 µl of test substance (BsOIL or BsLPRE or BcLPRE or BsVOIL, different boswellic acids and positive control Neostigmin) at various concentrations and 20 µl of (100 mU/mL) enzyme. For blanks, enzyme was replaced with phosphate buffer. The reaction mixture was mixed thoroughly, 100 µl of Ellman's reagent was added and incubated at room temperature for 10 min. The absorbance was measured at 412 nm using microplate reader. The percentage inhibition of enzyme activity was calculated by comparing OD's of tests wells with that of control wells using the following formula. Calculations: % inhibition=[(control–sample)/control]×100. The results of Acetylcholinesterase inhibitory activity of BsOIL, BsLPRE, BcLPRE, BsVOIL and boswellic acids are summarized in Table 2 and 3.

TABLE 2

Acetylcholinesterase inhibitory activity of BsOIL, BsLPRE, BcLPRE, BsVOIL

| Name of the compound | % Inhibition at concentrations of | | | IC50 ng/mL |
|---|---|---|---|---|
| | 10 ng | 25 ng | 50 ng | |
| BsOIL | 10.65 | 17.09 | 32.69 | >50 |
| BsLPRE | 31.5 | 43.7 | 57.87 | 37.01 |
| BcLPRE | 15.6 | 23.18 | 42.56 | >50 |
| BsVOIL | 16.5 | 25.49 | 33.01 | >50 |
| BSE-85 | — | 4.22 | 6.27 | |
| Composition-1 | | | | 42.7 |
| Neostigmin | 25.17 | 37.19 | 54.69 | 43.29 |

TABLE 3

Acetylcholinesterase inhibitory activity of Pure Boswellic acids

| Name of the Product | % Inhibition at concentrations of | | | | IC50 ng/mL |
|---|---|---|---|---|---|
| | 10 ng | 25 ng | 50 ng | 100 ng | |
| 11-keto-β-boswellic acid | — | 11.82 | 16.36 | 24.55 | >100 |
| 3-O-acetyl-11-keto-β-boswellic acid | — | 9.64 | 16.07 | 27.5 | >100 |
| α-boswellic acid | — | 13.85 | 21.92 | 39.23 | >100 |
| β-boswellic acid | — | 16.75 | 21.23 | 31.37 | >100 |
| 3-O-acetyl-α-boswellic acid | — | 14.86 | 21.28 | 33.11 | >100 |
| 3-O-acetyl-β-boswellic acid | — | 36.29 | 40.32 | 52.02 | 91.77 |
| Neostigmin | 25.17 | 37.19 | 54.69 | — | 43.29 |

Example 7

Acetylcholine Esterase Inhibitory Activity of BsOIL, BsLPRE, BcLPRE, BsVOIL and Boswellic Acids in PC 12 Cells The inhibitory property on the enzyme activity was assessed in β-amyloid peptide induced-rat pheochromocytoma PC 12 cells. Rat pheochromocytoma PC 12 cells were equally distributed with phenol red free Dulbecco's modified Eagle's red medium (DMEM) (Sigma Life Science, USA) containing 10% fetal bovine serum (FBS) in 24-well plate. Cells were pretreated with test agents (BsOIL, BsLPRE, BcLPRE, BsVOIL and different boswellic acids and positive control Neostigmin) for 1 h. Thereafter, cells were induced with 1 µg/mL of β-amyloid peptide (Calbiochem, USA) for 24 h at 37° C. After 24 h, cells were collected and washed twice with 1×PBS by centrifugation at 1200 rpm for 5 min at 4° C. Cell extracts were prepared in solubilization buffer (10 mM Tris, pH 7.2; 100 mM NaCl, 50 mM MgCl2, 1% Triton X-100). The cell extracts were used as samples for measuring the acetylcholine esterase (AChE) activity.

Cell extract samples (100 µl) were dispensed into each well of 96-well microtitre plate. Fifty micro liters of DTNB (Dithiobisnitro benzoate) solution was added to each well and incubated for 5 min at room temperature. After incubation, 50 µl of acetyl choline iodide solution was added to each well and absorbance was read immediately at 405 nm for 12 min at 2 min intervals. A standard curve was constructed by using serial concentrations of acetyl cholinesterase (0-100 mU). Total protein present in 100 µl aliquot of cell extract was calculated by Bradford method and the enzyme activity was normalized and expressed as unit activity per milligram of protein. Efficacy of test samples was expressed in terms of percent inhibition of AChE activity and compared with a standard drug, Neostigmin as the positive control.

Results: Table 4 and Table 5 are summary of the acetyl cholinesterase inhibitory activities exhibited by various non acidic extracts from *Boswellia serrata* and *Boswellia carterii* (BsOIL, BsLPRE, BcLPRE and BsVOIL) and different boswellic acids. A standard drug, Neostigmin was used as the positive control for comparing the AChE inhibitory efficacies of the boswellia products.

TABLE 4

Acetyl cholinesterase inhibitory property of BsOIL, BsLPRE, BcLPRE and BsVOIL

| Test samples | Treatment Conc. | % inhibition in AChE activity |
|---|---|---|
| BsOIL | 100 ng/ml | 19.92 |
| BsLPRE | 100 ng/mL | 25.31 |
| BcLPRE | 100 ng/mL | 18.67 |
| BsVOIL | 100 ng/mL | 16.46 |
| Neostigmin | 20 ng/ml | 49.09 |

TABLE 5

Comparative efficacy of different boswellic acids in inhibiting Acetyl cholinesterase activity

| Test samples | Treatment Conc. | % inhibition in AChE activity |
|---|---|---|
| 11-keto-β-boswellic acid | 100 ng/ml | 31.39 |
| 3-O-acetyl-keto-β-boswellic acid | 100 ng/ml | 41.67 |
| α-boswellic acid | 100 ng/ml | 38.42 |
| β-boswellic acid | 100 ng/ml | 46.54 |
| 3-O-acetyl-α-boswellic acid | 100 ng/ml | 29.22 |
| 3-O-acetyl-β-boswellic acid | 100 ng/ml | 37.34 |
| Neostigmin | 20 ng/ml | 54.65 |

Example 8

Preparation of Composition-1

Composition-1 was prepared by mixing unit doses of the following components; four parts of *Boswellia serrata* low polar gum resin extract (BsLPRE) (4 g) and one part of *Boswellia serrata* extract standardized to 85% total Boswellic acids (BSE 85%) (1 g).

Example 9

Composition-2

Composition-2 was prepared by mixing unit doses of the following components; one part of *Boswellia serrata* volatile oil (BsVOIL) (1 g) and four parts of *Boswellia serrata* extract standardized to 85% total Boswellic acids (BSE 85%) (4 g).

Example 10

Composition-3

Composition-3 was prepared by mixing unit doses of the following components; one part of *Boswellia serrata* non acidic oil (BsOIL) (1 g) and four parts of *Boswellia serrata* extract standardized to 85% total Boswellic acids (BSE 85%) (4 g).

Example 11

Composition-4

Composition-4 was prepared by mixing unit doses of the following components; one part of *Boswellia carterii* low polar gum resin extract (BcLPRE) (1 g) and four parts of *Boswellia serrata* extract standardized to 85% total Boswellic acids (BSE 85%) (4 g).

Example 12

Composition-5

Composition-5 was prepared by mixing unit doses of the following components; one part of *Boswellia carterii* volatile oil (BcVOIL) (1 g) and three parts of *Boswellia carterii* extract standardized to 85% total Boswellic acids (BCE 85%) (3 g).

Example 13

Composition-6

Composition-6 was prepared by mixing unit doses of the following components; one part of *Boswellia serrata* low polar gum resin extract (BsLPRE) (1 g), four parts of *Boswellia serrata* extract enriched with 20% of 3-O-acetyl-11-keto-13-Boswellic acid (AKBA) (4 g).

Example 14

Composition-7

Composition-7 was prepared by mixing unit doses of the following components; one part of *Boswellia carterii* low polar gum resin extract (BcLPRE) (1 g), four parts of *Boswellia carterii* extract enriched with 20% of 3-O-acetyl-11-keto-13-Boswellic acid (AKBA) (4 g).

Example 15

Composition-8

Composition-8 was prepared by mixing unit doses of the following components; one part of *Boswellia serrata* low polar gum resin extract (BsLPRE) (1 g), four parts of *Boswellia serrata* extract enriched with 40% of 3-O-acetyl-11-keto-13-Boswellic acid (AKBA) (4 g).

Example 16

Composition-9

Composition-9 was prepared by mixing unit doses of the following components; one part of *Boswellia carterii* low polar gum resin extract (BcLPRE) (1 g), three parts of *Boswellia carterii* extract enriched with 40% of 3-O-acetyl-11-keto-13-Boswellic acid (AKBA) (3 g).

Example 17

Composition-10

Composition-10 was prepared by mixing unit doses of the following components; one part of *Boswellia serrata* low polar gum resin extract (BsLPRE) (1 g) and three parts of *Bacopa monniera* standardized extract (3 g).

Example 18

Composition-11

Composition-10 was prepared by mixing unit doses of the following components; one part of *Boswellia serrata* volatile oil fraction (BsVOIL) (1 g) and three parts of *Bacopa monniera* standardized extract (3 g).

Example 19

Composition-12

Composition-12 was prepared by mixing unit doses of the following components; one part of non-acidic *Boswellia serrata* oil fraction (BsOIL) (1 g) and three parts of *Bacopa monniera* standardized extract (3 g).

Example 20

Composition-13

Composition-13 was prepared by mixing unit doses of the following components; one part of *Boswellia serrata* low polar gum resin extract (BsLPRE) (1 g) and four parts of *Bacopa monniera* water extract (4 g).

Example 21

Composition-14

Composition-14 was prepared by mixing unit doses of the following components; one part of *Boswellia serrata* low polar gum resin extract (BsLPRE) (1 g) and four parts of *Bacopa monniera* 90% methanol extract (4 g).

Example 22

Composition-15

Composition-15 was prepared by mixing unit doses of the following components; one part of *Boswellia serrata* low polar gum resin extract (BsLPRE) (1 g) and three parts of *Bacopa monniera* standardized extract (3 g).

Example 23

Composition-16

Composition-16 was prepared by mixing unit doses of the following components; one part of *Boswellia serrata* low polar gum resin extract (BsLPRE) (1 g) and four parts of *Bacopa monniera* extract standardized to 25% bacopasaponins (4 g).

Example 24

Composition-17

Composition-17 was prepared by mixing unit doses of the following components; one part of *Boswellia carterii* low polar gum resin extract (BcLPRE) (1 g) and four parts of *Bacopa monniera* extract standardized to 25% bacopasaponins (4 g).

Example 25

Composition-18

Composition-18 was prepared by mixing unit doses of the following components; one part of *Boswellia papyrifera* low polar gum resin extract (BpLPRE) (1 g) and four parts of *Bacopa monniera* extract standardized to 25% bacopasaponins (4 g).

Example 26

Composition-19

Composition-19 was prepared by mixing unit doses of the following components; one part of *Boswellia serrata* low polar gum resin extract (BsLPRE) (1 g) and four parts of *Curcuma longa* extract standardized to 95% total Curcuminoids (CLE 95%) (1 g).

Example 27

Composition-20

Composition-20 was prepared by mixing unit doses of the following components; one part of *Boswellia serrata* volatile oil fraction (BsVOIL) (1 g) and four parts of *Curcuma longa* extract standardized to 95% total Curcuminoids (CLE 95%) (4 g).

Example 28

Composition-21

Composition-21 was prepared by mixing unit doses of the following components; one part of non-acidic *Boswellia serrata* oil fraction (BsOIL) (1 g) and four parts of *Curcuma longa* extract standardized to 95% total Curcuminoids (CLE 95%) (4 g).

Example 29

Composition-22

Composition-22 was prepared by mixing unit doses of the following components; one part of *Boswellia serrata* low polar gum resin extract (BsLPRE) (1 g) and three parts of curcumin (3 g).

Example 30

Composition-23

Composition-23 was prepared by mixing unit doses of the following components; one part of *Boswellia serrata* low polar gum resin extract (BsLPRE) (1 g) and three parts of bisdemethylcurcumin (BDMC) (3 g).

Example 31

Composition-24

Composition-24 was prepared by mixing unit doses of the following components; one part of *Boswellia serrata* low polar gum resin extract (BsLPRE) (1 g) and four parts of *Withania somnifera* methanol extract (4 g).

Example 32

Composition-25

Composition-25 was prepared by mixing unit doses of the following components; one part of *Boswellia carterii* low polar gum resin extract (BcLPRE) (1 g) and four parts of standardized *Withania somnifera* extract (4 g).

Example 33

Composition-26

Composition-26 was prepared by mixing unit doses of the following components; one part of *Boswellia* low polar gum resin extract (BLPRE) (1 g) and four parts of standardized *Rosmarinus officinalis* extract (4 g).

Example 34

Composition-27

Composition-27 was prepared by mixing unit doses of the following components; one part of *Boswellia serrata* low polar gum resin extract (BsLPRE) (1 g) and four parts of standardized *Rosmarinus officinalis* extract (4 g).

Example 35

Composition-28

Composition-28 was prepared by mixing unit doses of the following components; one part of *Boswellia carterii* low polar gum resin extract (BcLPRE) (1 g) and four parts of standardized *Rosmarinus officinalis* extract (4 g).

Example 36

Composition-29

Composition-29 was prepared by mixing unit doses of the following components; one part of *Boswellia serrata* low polar gum resin extract (BsLPRE) (1 g) and four parts of *Rosmarinus officinalis* extract standardized to 30% Rosmarinic acid (RA 30%) (4 g).

Example 37

Composition-30

Composition-30 was prepared by mixing unit doses of the following components; one part of *Boswellia carterii* low polar gum resin extract (BcLPRE) (1 g) and three parts of *Rosmarinus officinalis* extract standardized to 30% Rosmarinic acid (RA 30%) (3 g).

Example 38

Composition-31

Composition-31 was prepared by mixing unit doses of the following components; one part of *Boswellia* non acidic oil (BOIL) (1 g) and three parts of *Garcinia mangostana* methanol extract (3 g).

Example 39

Composition-32

Composition-32 was prepared by mixing unit doses of the following components; one part of non-acidic *Boswellia serrata* oil (BsOIL) (1 g) and three parts of *Garcinia mangostana* methanol extract (3 g).

Example 40

Composition-33

Composition-33 was prepared by mixing unit doses of the following components; one part of *Boswellia serrata* low polar gum resin extract (BsLPRE) (1 g) and three parts of *Garcinia mangostana* methanol extract (3 g).

Example 41

Composition-34

Composition-34 was prepared by mixing unit doses of the following components; two parts of *Boswellia serrata* low polar gum resin extract (BsLPRE) (2 g) and one part of α-mangostin (1 g).

Example 42

Composition-35

Composition-35 was prepared by mixing unit doses of the following components; four parts of *Boswellia serrata* low polar gum resin extract (BsLPRE) (4 g) and one part of α-mangostin (1 g).

Example 43

Composition-36

Composition-40 was prepared by mixing unit doses of the following components; one part of *Boswellia* low polar gum resin extract fraction (BLPRE) (1 g) and three parts of *Sphaeranthus indicus* ethyl acetate extract (3 g).

Example 44

Composition-37

Composition-40 was prepared by mixing unit doses of the following components; one part of non acidic *Boswellia* oil fraction (BOIL) (1 g) and four parts of *Sphaeranthus indicus* ethyl acetate extract (4 g).

Example 45

Composition-38

Composition-40 was prepared by mixing unit doses of the following components; one part of *Boswellia* volatile oil fraction (BVOIL) (1 g) and four parts of *Sphaeranthus indicus* ethyl acetate extract (4 g).

Example 46

Assay for Measuring Reactive Oxygen Species (ROS)

Formation of ROS was measured using of the fluorescent probe DCFH-DA. The method is based on the incubation of the RAW 264.7 mouse macrophages with DCFH-DA, which diffuses passively through the cellular membrane. Intracellular esterase activity results in the formation of DCFH, which emits fluorescence when oxidized to 20, 70-dichlorofluorescein (DCF). Briefly, the cells (final concentration $2\times10^6$/ml suspension) were incubated with DCFH-DA (5 mM) in HEPES-buffered (20 mM) HBSS ($CaCl_2$ 1.26 mM, KCL 5.37 mM, $KH_2PO_4$ 0.44 mM; $MgCl_2$ 0.49 mM, $MgSO4$ 0.41 mM, NaCl 140 mM, $NaHCO_3$ 4.17 mM, $Na_2HPO_4$ 0.34 mM) with glucose (5 mM) at 37° C. for 15 mM Following centrifugation, the extracellular buffer with DCFH-DA was exchanged with fresh buffer and the suspension was mixed gently. The cells ($2\times10^6$/ml, 125 ml) were transferred to 250 ml wells (microtiter plate reader, 96 wells) containing 125 ml buffer with the different concentrations of test samples (α-mangostin, BsLPRE, Composition-34 and Composition-35) in presence or absence of 100 mM $H_2O_2$. Fluorescence was recorded using excitation wavelength 485 nm, emission wavelength 530 nm in a Modulus luminescence spectrometer (Turner Biosystems, USA) for 120 mM Results are calculated as area under the curve (AUC) and the percentage of inhibition of intracellular ROS generation was calculated from the cultures treated with $H_2O_2$. The results are summarized in Table 6.

TABLE 6

Anti-oxidant properties of herbal products and their combinations

| Serial no | Treatments | Inhibition of Reactive Oxygen Species (ROS) generation (IC50) |
|---|---|---|
| 1 | α-mangostin | 49.817 ug/ml |
| 2 | BsLPRE | 53.879 ug/ml |
| 3 | Composition-34 | 33.342 ug/ml |
| 4 | Composition-35 | 50.776 ug/ml |

Example 47

Cell Proliferation Assay

Effect of BsLPRE or α-mangostin or their combination (Composition-34) on cell growth was tested in oxidative stress induced IMR32 human neuroblastoma cells SW 982 human synovial cells by using MTT based cell proliferation assay. Briefly, IMR32 human neuroblastoma cells were cultivated in Dulbecco's modified Eagle's red medium (DMEM) (Sigma Life Science, USA) containing 10% fetal bovine serum (FBS). Equal number of IMR32 cells was seeded in to each well of 96 well microplate and incubated at 37° C. with 5% $CO_2$. The cells were treated with 250 µM $H_2O_2$ in presence or absence of different concentrations of BsLPRE or α-mangostin or their combination (Composition-34) for 72 h. Control wells were supplemented with 0.05% DMSO. After 72 h of treatment, equal volume of MTT reagent (R&D Systems, USA) was added to each well and incubated for 4 h. Thereafter, 50 µl of solublization buffer (R&D Systems, USA) was added to each well to solubilize the colored formazan crystals produced by the reduction of MTT. After 24 h, the optical density was measured at 550 nm using microplate reader (Bio-Rad, USA). In each assay, the vehicle control and the treatments were done in quadruplicates. The average OD obtained in the vehicle control wells is considered as the cell proliferation index of 100. The results are summarized in Table-7 below.

TABLE 7

Protection from oxidative stress induced cytotoxic damage of human neuroblastoma cells

| S. No | Treatments | Treatment conc. | Cell proliferation Index |
|---|---|---|---|
| 1 | Vehicle Control |  | 100.00 |
| 2 | H2O2 | 250 uM | 78.71 |
| 3 | α-mangostin | 10 ng/ml | 80.32 |
|  |  | 25 ng/ml | 86.78 |
|  |  | 50 ng/ml | 87.21 |
|  |  | 100 ng/ml | 91.78 |
| 4 | BsLPRE | 10 ng/ml | 87.81 |
|  |  | 25 ng/ml | 92.24 |
|  |  | 50 ng/ml | 95.19 |
|  |  | 100 ng/ml | 97.30 |
| 5 | Composition-34 | 10 ng/ml | 92.81 |
|  |  | 25 ng/ml | 95.82 |
|  |  | 50 ng/ml | 99.05 |
|  |  | 100 ng/ml | 101.33 |

Example 48

Inhibition of acetylcholinesterase activity by herbal products and their combinations in Beta Amyloid protein induced PC12 cells: The acetylcholinesterase inhibitory activity of α-mangostin, BsLPRE and Composition-34, recorded in Table 8, was measured using the procedure described in example 7.

TABLE 8

Inhibition of acetylcholinesterase activity by herbal products

| Serial No. | Treatments | Treatment conc. | % inhibition in Acetylcholinesterase (AChE) activity |
|---|---|---|---|
| 1 | α-mangostin | 100 ng/ml | 26.83 |
|  |  | 250 ng/ml | 29.48 |
| 2 | BsLPRE | 100 ng/ml | 30.99 |
|  |  | 250 ng/ml | 35.15 |
| 3 | Composition-34 | 100 ng/ml | 37.97 |
|  |  | 250 ng/ml | 40.57 |

Example 49

Determination of Spatial Learning and Memory Improvement Efficacy of BsLPRE in Rats Using Elevated Radial Arm Maze Method The animal study protocol was approved by institutional animal ethics committee. Sprague Dawley rats were acclimatized for one week and healthy rats were selected for the study. The selected rats were pre-trained in elevated radial arm maze (RAM) adapted rats were allocated to various treatment groups each containing eight rats. After completion of pre-training, the oral treatment was initiated to the animals and continued daily up to two weeks. During this treatment phase the rats were placed on the RAM for 10 min each to recognize the food pellets present in the three different colored arms. During training the spatial learning was estimated by measuring various parameters like number of days required to learn the task, latency in finding food and number of wrong entries/attempts. After this treatment and training the animals were given rest without treatment or training for one week ($3^{rd}$ week). On $4^{th}$ week, the animals were treated with allocated doses of test products and memory retention test was assessed using the same animals by measuring latency and number of wrong entries. The data was analyzed using ANOVA followed by a suitable post-hoc test.

Result (Spatial Learning):

Oral administration of BsLPRE (250 mg/kg) significantly ($P<0.01$) decreased the number of days required to make the rats learned as per set criteria and significantly ($P<0.05$) decreased the time taken to find the food by the learned rats in the elevated RAM model. Piracetam showed significant improvement in spatial learning represented by reduction in latency and Number of wrong entries, when compared with the control group and the results are as stated below (FIG. 5A to 5C). The test product BsLPRE also significantly improves cognition and memory retention (FIGS. 6A and 6B). These results suggest that the use of BsLPRE improves spatial learning and memory retention. According to these findings, BsLPRE is a promising candidate for facilitation of learning and memory.

Example 50

Preparation of *Boswellia carterii* Low Polar Gum Resin Extract (BcLPRE)

The *Boswellia carterii* gum resin (100 g) was dispersed in 600 mL of methyl iso butyl ketone (MIBK) solvent and stirred at room temperature for 60 min The insoluble gum materials were separated by filtration. The MIBK solution was extracted repeatedly with 2% KOH solution (3×200 mL) to remove the acidic compounds. The MIBK layer was then washed successively with water (400 mL) and brine (200 mL). The MIBK layer was evaporated under reduced pressure at 60-70° C. and the volatile components are then removed from the oily residue under vacuum at 75-85° C. to obtain *Boswellia carterii* low polar gum resin extract or BcLPRE as a viscous oil (9.5 g).

Alternatively, the gum resin (250 g) collected from *Boswellia carterii* was extracted with methanol (300 mL×3) and the combined methanol extract was concentrated. The residue (50 g) was dissolved in ethyl acetate (400 mL) and extracted thrice with 1N KOH (3×100 mL). The organic layer was washed with water (2×200 mL) and brine (200 mL) and evaporated to obtain *Boswellia* oil. The volatile compounds were evaporated from the oil under vacuum at 75-85° C. to obtain 17.75 g of BcLPRE.

Example 51

Comparative Bioavailability of 3-O-acetyl-11-keto-β-boswellic Acid (AKBA) from Different Boswellia Products Albino Wistar rats were quarantined and healthy rats were selected for the study. The selected animals were acclimatized for 7 days prior to the study initiation in the allocated room Animals employed for the study were randomized into various treatment groups, fasted overnight at free access to water, body weights were noted and individual doses were calculated based on the body weights. Blood samples were collected from all animals prior to oral administration of test products and at 0.5, 1, 2, 4, 8 and 12 hrs after oral administration. Collected blood samples were allowed to clot for 10 min and centrifuged at 4° C. at 1800 g for 10 min The serum samples were deproteinized with 100 μL TCA (20%) and 1.8 mL of HPLC grade methanol, centrifuged at 4° C. at 1800 g for 10 min and supernatants were subjected to LCMS analysis for total AKBA. The Composition LI 13108F comprising *Boswellia serrata* extract selectively enriched to 30% 3-O-acetyl-11-keto-β-boswellic acid (AKBA) (LI 13115) and *Boswellia serrata* non-volatile oil (BsLPRE) in the ratio 2:1; and composition LI13119F comprising *Boswellia serrata* extract standardized to 30% AKBA and *Boswellia serrata* steam distilled oil (BVOIL) in the ratio 2:1 showed better oral bioavailability with Area under the curve (AUC) 14.08 and 11.23 respectively compared to individual *Boswellia serrata* extract standardized to 30% AKBA (LI 13115) (AUC: 9.825). The bioavailability [in terms of [AUC] of LI 13108F is 43.33% more than LI 13115. The bioavailability of LI 13119F is 14.33% more than that of LI 13115. The serum concentration of AKBA in animals of various treatment groups at various time points was summarized in Table 9. The serum concentration against time was plotted and the details are summarized in FIG. 7.

TABLE 9

Serum concentration of AKBA
Mean Serum AKBA concentration μg/mL

| Time (h) | LI 13115 (Mean ± SE) | LI 13108F (Mean ± SE) | LI 13119F (Mean ± SE) |
|---|---|---|---|
| 0 | 0.000 ± 0.00 | 0.000 ± 0.00 | 0.000 ± 0.00 |
| 0.5 | 1.200 ± 0.19 | 1.533 ± 0.06 | 1.805 ± 0.21 |
| 1 | 1.545 ± 0.28 | 1.853 ± 0.11 | 1.865 ± 0.32 |
| 2 | 1.980 ± 0.45 | 2.000 ± 0.16 | 1.750 ± 0.26 |

TABLE 9-continued

Serum concentration of AKBA
Mean Serum AKBA concentration μg/mL

| Time (h) | LI 13115 (Mean ± SE) | LI 13108F (Mean ± SE) | LI 13119F (Mean ± SE) |
|---|---|---|---|
| 4 | 0.850 ± 0.32 | 2.147 ± 0.41 | 1.100 ± 0.07 |
| 8 | 0.452 ± 0.22 | 0.520 ± 0.16 | 0.645 ± 0.13 |
| 12 | 0.095 ± 0.10 | 0.199 ± 0.14 | 0.200 ± 0.20 |
| AUC | 9.825 | 14.0825 (43.33%) | 11.2325 (14.33%) |

Example 52

Comparative Bioavailability of LI01008 and its Composition

LI13124F1 Animals (Wistar Rats) were acclimatized for 7 days prior to study initiation. Six animals were divided randomly into 2 groups, each comprised of 3 animals. The body weights were noted and doses were calculated based on initial body weights. Animals were treated orally with 450 mg dose of a composition (LI13124F1) containing bisdemethylcurcumin (LI01008) and BsLPRE (LI13115) in 2:1 ratio or 300 mg/kg LI01008 as suspension in 0.5% CMC. Blood samples were collected before treatment and several time intervals after treatment at 0.5, 1, 2, 4, 6, 8 and 12 hours, as plotted in FIG. 8. Collected blood samples were processed in a refrigerated centrifuge and serum samples were deproteinized using HPLC grade methanol, mixed thoroughly and centrifuged to remove precipitated proteins clear supernatants were subjected for LI01008 estimation by HPLC. The data is summarized in table 10 below.

As per the data, the bioavailability of LI01008 in the composition LI13124F1 is 75% better compared to that when LI01008 is administered alone.

TABLE 10

Serum concentration of bisdemethylcurcumin

| S. No | Time after Admn. | LI13124F1 suspension in 0.5% CMC | LI01008 suspension in 0.5% CMC |
|---|---|---|---|
| 1 | 0 | 0 | 0 |
| 2 | 0.5 | 0.1075 | 0.07 |
| 3 | 1 | 0.16 | 0.1085 |
| 4 | 2 | 0.105 | 0.078 |
| 5 | 4 | 0.065 | 0.035 |
| 6 | 6 | 0.032 | 0.00535 |
| 7 | 8 | 0.0085 | 0 |
| 8 | 12 | 0 | 0 |

It will be appreciated to those of ordinary skill in the art that changes could be made to the embodiments described above without departing from the broad inventive concept thereof. It is understood, therefore, that this invention is not limited to the particular embodiments or examples disclosed, but is intended to cover modifications within the objectives and scope of the present invention.

What is claimed is:

1. A dosage form comprising at least one non-acidic extract derived from a *Boswellia* species in an amount effective to enhance a cognitive function in an individual in need thereof, said non-acidic extract being prepared by a process comprising:
    i) extraction of a *Boswellia* gum resin with a water-immiscible non-polar solvent to produce a non-polar solvent extract;

ii) washing the non-polar solvent extract with aqueous alkali to remove boswellic acids from the non-polar solvent extract to produce an intact *Boswellia* oil (BOIL); and
iii) subjecting said BOIL to distillation to produce a non-volatile *Boswellia* oil component and a *Boswellia* volatile oil (BVOIL) recovered as a distillate from said distillation;
wherein said non-acidic extract is selected from the group consisting of the non-volatile *Boswellia* oil component, BVOIL, BOIL, and a mixture thereof.

2. A composition comprising a bio-enhancing agent and a biological agent, wherein said composition contains said bio-enhancing agent in an amount which is effective for enhancing the bioavailability of said biological agent;
said bio-enhancing agent being a non-acidic extract derived from the gum resin of a *Boswellia* species for enhancing the bioavailability of biological agents;
said non-acidic extract being prepared by a process comprising:
i) extraction of a *Boswellia* gum resin with a water-immiscible non-polar solvent to produce a non-polar solvent extract;
ii) washing the non-polar solvent extract with aqueous alkali to remove boswellic acids from the non-polar solvent extract to produce an intact *Boswellia* oil (BOIL); and
iii) subjecting said BOIL to distillation to produce a non-volatile *Boswellia* oil component and a *Boswellia* volatile oil (BVOIL) recovered as a distillate from said distillation;
wherein said non-acidic extract is selected from the group consisting of the non-volatile *Boswellia* oil component (BLPRE), BVOIL, BOIL, and a mixture thereof.

3. The dosage form of claim 1, wherein said dosage form is effective for treatment of a cognitive disorder, said dosage form further comprising a nootropic agent selected from the group consisting of:

at least one extract selected from the group consisting of *Bacopa monnieri, Withania somnifera, Emblica officinalis, Centella asiatica*; and at least one phytochemical selected from the group consisting of Bacoside A3, Bacopaside II, Jujubogenin isomer of bacopasaponin C, Bacopasaponin C, Bacopaside I, Bacosine, Apigenin, Luteolin and Sitosterol-D-glucoside, carnosic acid, rosmarinic acid, camphor, caffeic acid, ursolic acid, betulinic acid, rosmaridiphenol, rosmanol, salts thereof, and mixtures thereof;

said dosage form being free of boswellic acids.

4. The dosage form of claim 1, wherein said dosage form is effective for treatment of a cognitive disorder, said cognitive disorder being selected from the group consisting of impaired memory, senile dementia, multi-infarct dementia, dyslexia, aphasia, myasthenia gravis, vascular dementia, mild cognitive impairment (MCI), Attention-deficient Hyperactivity Disorder (ADHD), Lewy body dementia, Wemicke-Korsakoff-syndrome, Alzheimer's, Parkinson's disease, hypoxia, anoxia, cerebrovascular insufficiency, epilepsy, myoclonus and hypocholinergic dysfunctions, and neurodegenerative disorders.

5. The dosage form of claim 4, wherein said cognitive disorder is impaired memory.

6. The dosage form of claim 1, wherein said dosage form comprises said non-acidic extract and at least one component selected from the group consisting of a biological agent, a phytochemical, a vitamin, an amino acid, a mineral, a pharmaceutically acceptable excipient, a pharmaceutically acceptable vehicle, a pharmaceutically acceptable carrier, a pharmaceutically acceptable diluent, and a mixture thereof.

7. The dosage form of claim 4, wherein said dosage form comprises said non-acidic extract and at least one component selected from the group consisting of a biological agent, a phytochemical, a vitamin, an amino acid, a mineral, a pharmaceutically acceptable excipient, a pharmaceutically acceptable vehicle, a pharmaceutically acceptable carrier, a pharmaceutically acceptable diluent, and a mixture thereof.

8. The dosage form of claim 1, wherein said *Boswellia* species is selected from the group consisting of *Boswellia serrata, Boswellia carterii, Boswellia papyrifera, Boswellia ameero, Boswellia bullata, Boswellia dalzielii, Boswellia dioscorides, Boswellia elongata, Boswellia frereana, Boswellia nana, Boswellia neglecta, Boswellia ogadensis, Boswellia pirottae, Boswellia popoviana, Boswellia rivae, Boswellia sacra, Boswellia socotrana*, and mixtures thereof.

9. The dosage form according to claim 4, wherein said dosage form comprises said biological agent, said biological agent being selected from the group consisting of dietary supplements, herbal ingredients, nutraceuticals, functional ingredients, functional foods, nootropic agents, and mixtures thereof.

10. The dosage form according to claim 4, wherein said biological agent is selected from the group consisting of natural antioxidants, neuroprotecting agents, anti-inflammatory agents, immune modulators, and mixtures thereof.

11. The dosage form according to claim 4, wherein said dosage form comprises said biological agent, said biological agent being selected from the group consisting of:

at least one *Boswellia serrata* extract containing at least one boswellic acid, a boswellic acid compound, and a mixture thereof.

12. The dosage form according to claim 4, wherein said dosage form comprises said biological agent, said biological agent being:

at least one *Boswellia serrata* extract containing between about 20% and about 100% by weight of total boswellic acids.

13. The dosage form according to claim 4, wherein said dosage form comprises said biological agent, said biological agent being selected from the group consisting of:

at least one Curcuma longa extract containing at least one curcuminoid, a curcuminoid compound, and a mixture thereof.

14. The dosage form according to claim 4, wherein said dosage form comprises said biological agent, said biological agent being selected from the group consisting of;

at least one nootropic agent selected from the group consisting of:

at least one extract selected from the group consisting of *Bacopa monnieri*, Withania somnifera, Emblica officinalis, Centella asiatica;

at least one phytochemical selected from the group consisting of Bacoside A3, Bacopaside II, Jujubogenin isomer of bacopasaponin C, Bacopasaponin C, Bacopaside I, Bacosine, Apigenin, Luteolin and Sitosterol-D-glucoside, curcumin, demethoxycurcumin, bisdemethoxycurcumin, monodemethylcurcumin, bisdemethylcurcumin, tetrahydrocurcumin, tetrahydrodemethoxycurcumin, tetrahydrobisdemethoxycurcumin and ar-turmerone, carnosic acid, rosmarinic acid, camphor, caffeic acid, ursolic acid, betulinic acid, rosmaridiphenol, rosmanol, salts thereof, and mixtures thereof.

15. The dosage form according to claim 4, wherein said excipients are selected from the group consisting of surfactants, binders, disintegrators, lubricants, preservatives, stabilizers, buffers and suspensions.

16. The dosage form of claim 1, wherein said dosage form is an oral dosage form.

17. The dosage form of claim 1, wherein said dosage form is a controlled release dosage form.

18. A method for improving mental condition by slowing down memory deterioration in an individual in need thereof, comprising:
    administering a composition according to claim 1 to said individual;
    wherein said composition improves said mental condition.

19. A method of enhancing brain functions selected from the group consisting of cognition, memory, learning, communication in an individual in need thereof, comprising:
    administering a composition according to claim 1 to said individual;
    wherein said brain function is enhanced.

20. The composition according to claim 2, wherein said *Boswellia* species is selected from the group consisting of *Boswellia serrata, Boswellia carterii, Boswellia papyrifera*, and mixtures thereof.

21. The composition according to claim 2, wherein said composition contains said bio-enhancing agent in an amount which is effective for enhancing the bioavailability of said biological agent in a warm blooded animal in need thereof.

22. The bio-enhancing composition according to claim 21, wherein said biological agent is at least one agent selected from the group consisting of a biologically active ingredient, a functional ingredient, an herbal ingredients, a dietary supplement, a nutrient, an antioxidant, a vitamin, a mineral, an amino acid, an oil, and mixtures thereof.

23. The bio-enhancing composition according to claim 1, wherein said biological agent comprises one or more ingredients selected from herbal ingredients, dietary supplements, antioxidants, vitamins, minerals, amino acids, fatty acids, essential oils, fish oils, enzymes, glucosamine, chondroitin and probiotics or their salts or mixtures.

24. The bio-enhancing composition according to claim 21, wherein said biological agent comprises a herbal ingredient selected from the group consisting of extracts or phytochemicals, said extracts or phytochemicals being derived from *Withania somnifera, Bacopa monniera, Boswellia species, Curcuma species, Centella asiatica, Sphaeranthus indicus, Garcinia mangostana, Annona squamosa, Holoptelia integrifolia, Piper betel, Dolichos biflorus, Moring a oleifera, Murraya koenigii*, and mixtures thereof.

25. The bio-enhancing composition according to claim 21, wherein said biological agent is derived from a *Boswellia* species, and includes one or more boswellic acids selected from the group consisting of α-boswellic acid, β-boswellic acid, 3-O-acetyl-β-boswellic acid, 3-O-acetyl-β-boswellic acid, 3-O-acetyl-11-keto-β-boswellic acid, and 3-O-acetyl-11-keto-β-boswellic acid.

26. The bio-enhancing composition according to claim 24, wherein the herbal ingredient is derived from a *Boswellia* species, and includes an extract comprising 3-O-acetyl-11-keto-β-boswellic acid.

27. The bio-enhancing composition according to claim 24, wherein the herbal ingredient is derived from a *Curcuma* species, and includes a component selected from the group consisting of curcumin, demethoxycurcumin, bisdemethoxycurcumin, monodemethylcurcumin, bis demethylcurcumin, tetrahydrocurcumin, tetrahydrodemethoxy-curcumin, tetrahydrobisdemethoxy-curcumin, ar-turmerone and mixtures thereof.

28. The bio-enhancing composition according to claim 24, wherein the herbal ingredient is derived from a *Curcuma* species, and includes curcumin.

29. The bio-enhancing composition according to claim 22, wherein the antioxidant comprises one or more ingredients selected from the group consisting of vitamin A, vitamin C, vitamin E, alpha-carotene, trans-beta-carotene, betacryptoxanthin, lycopene, lutein, zeaxanthin, pine bark bioflavonals complex, germanium, selenium and zinc.

30. The bio-enhancing composition according to claim 22, wherein the vitamin comprises:
    a water-soluble vitamin selected from the group consisting of vitamin B1, vitamin B2, niacinamide, vitamin B6, vitamin B12, folic acid, vitamin C, and mixtures thereof;
    a fat-soluble vitamin selected from the group consisting of vitamin A, vitamin D, vitamin E and vitamin K, and mixtures thereof; or
    a mixture of said water-soluble vitamin and said fat-soluble vitamin.

31. The bio-enhancing agent or composition according to claim 22, wherein the mineral comprises one or more minerals selected from the group consisting of calcium, iron, zinc, vanadium, selenium, chromium, iodine, potassium, manganese, copper, and magnesium.

32. The bio-enhancing agent or composition according to claim 22, wherein the amino acid comprises one or more amino acids selected from the group consisting of lysine, isoleucine, leucine, threonine, valine, tryptophan, phenylalanine, methionine, and 1-selenomethionine.

33. The bio-enhancing agent or composition according to claim 22, wherein the oil comprises one or more oils selected from the group consisting of omega-3 fatty acids, flaxseed oil, fish oils, essential oils and volatile oils.

34. The composition according to claim 2, wherein said *Boswellia* species is selected from the group consisting of *Boswellia ameero, Boswellia bullata, Boswellia dalzielii, Boswellia dioscorides, Boswellia elongata, Boswellia frereana, Boswellia nana, Boswellia neglecta, Boswellia ogadensis, Boswellia pirottae, Boswellia popoviana, Boswellia rivae, Boswellia sacra* and *Boswellia socotrana*.

35. A method for inhibiting beta-amyloid plaque deposition, comprising:
    administering an effective amount of a composition according to claim 1 to said individual;
    wherein said plaque deposition is inhibited.

* * * * *